US008715655B2

(12) United States Patent
Torikai et al.

(10) Patent No.: US 8,715,655 B2
(45) Date of Patent: May 6, 2014

(54) HUMAN ANTI-α9 INTEGRIN ANTIBODY

(75) Inventors: Masaharu Torikai, Kumamoto (JP);
Daisuke Ishikawa, Kumamoto (JP);
Toshihiro Nakashima, Kumamoto (JP);
Hirofumi Higuchi, Kumamoto (JP);
Fumihiko Sakai, Tokyo (JP);
Nobuchika Yamamoto, Tokyo (JP);
Hirotada Fujita, Tokyo (JP); Katsunari Taguchi, Tokyo (JP)

(73) Assignee: Juridical Foundation The Chemo-Sero-Therapeutic Research Institute, Kumamoto-shi (JP)

( * ) Notice: Subject to any disclaimer, the term of this patent is extended or adjusted under 35 U.S.C. 154(b) by 0 days.

(21) Appl. No.: 12/810,939

(22) PCT Filed: Dec. 26, 2008

(86) PCT No.: PCT/JP2008/073825
§ 371 (c)(1),
(2), (4) Date: Oct. 4, 2010

(87) PCT Pub. No.: WO2009/084671
PCT Pub. Date: Jul. 9, 2009

(65) Prior Publication Data
US 2011/0014213 A1 Jan. 20, 2011

(30) Foreign Application Priority Data
Dec. 28, 2007 (JP) ................................ 2007-340203

(51) Int. Cl.
*A61K 39/395* (2006.01)
*C07K 16/00* (2006.01)
*C07K 16/46* (2006.01)
*C07K 16/28* (2006.01)
*G01N 33/53* (2006.01)

(52) U.S. Cl.
USPC .............. 424/130.1; 530/287.1; 530/387.3; 530/388.22; 424/134.1; 424/143.1; 435/7.1

(58) Field of Classification Search
None
See application file for complete search history.

(56) References Cited

U.S. PATENT DOCUMENTS

| 7,396,913 | B2 * | 7/2008 | DeVries et al. ............ 530/387.1 |
| 2002/0039745 | A1 | 4/2002 | Yednock et al. |
| 2008/0152653 | A1 * | 6/2008 | Kurotaki et al. .......... 424/143.1 |
| 2009/0252734 | A1 | 10/2009 | Kanayama et al. |

FOREIGN PATENT DOCUMENTS

| EP | 1 840 135 A1 | 10/2007 |
| WO | WO 2006/075784 A1 | 7/2006 |
| WO | WO 2006/105511 A1 | 10/2006 |
| WO | WO 2008/007804 A1 | 1/2008 |

OTHER PUBLICATIONS

Palmer et al., Sequence and tissue distribution of the integrin alpha 9 subunit, a novel partner of beta 1 that is widely distributed in epithelia and muscle. J Cell Biol Dec. 1993;123(5):1289-97).*
Millard et al. Integrin Targeted Therapeutics. Theranostics 2011, 1, 154-188.*
Angela Wang, et al., "Differential Regulation of Airway Epithelial Integrins by Growth Factors", Am. J. Respir. Cell Mol. Biol., vol. 15, No. 5, 1996, pp. 664-672.
Hongwei Rao, et al., "$\alpha_9\beta_1$ : A Novel Osteoclast Integrin That Regulates Osteoclast Formation and Function", Journal of Bone and Mineral Research, vol. 21, No. 10, 2006. pp. 1657-1665.
Guangwu Xu, et al., "Role of Osteopontin in Amplification and perpetuation of Rheumatoid Synovitis", The Journal of Clinical Investigation, vol. 115, No. 4, Apr. 2005, pp. 1060-1067.
Search Report issued Feb. 24, 2009, in International Application No. PCT/JP2008/073825, filed Dec. 26, 2008.
Supplementary European Search Report issued Jul. 10, 2012 in Patent Application No. EP 08 86 7627.
Nicholas. L. Meyers, "Antibody response elicited against empty reticuloendotheliosis virus particles in two inbred lines of chicken", Veterinary Microbiology, 36 (1993) 317-332, Elsevier Science Publishers B.V., Amsterdam.
M.A. Ramakrishnan, A.B. Pandey, KP. Singh, R. Singh & M.L. Mehrotra, "Immune response and protective efficacy in sheep immunized with hydroxylamine-inactivated bluetongue virus vaccine", Veterillnria Italiana, 41 (3), 149-155.
Sonja Potzsch, et al., "B Cell Repertoire Analysis Identifies New Antigenic Domains on Glycoprotein B of Human Cytomegalovirus which Are Target of Neutralizing Antibodies", PLoS Pathogens | www.plospathogens.org, Aug. 2011 , vol. 7, Issue 8, e1002172.

* cited by examiner

*Primary Examiner* — Maher Haddad
(74) *Attorney, Agent, or Firm* — Oblon, Spivak, McClelland, Maier & Neustadt, L.L.P.

(57) ABSTRACT

The present invention provides a human anti-α9 integrin antibody or an antibody fragment which specifically recognize human α9 integrin and mouse α9 integrin, inhibit interaction with their ligands, particularly, the antibody or antibody fragment which recognize loop regions of human and mouse α9 integrins, a gene encoding the antibody or antibody fragment, a recombinant expression vector containing the gene, a transformant harboring the gene, production method of human anti-α9 integrin antibody or antibody fragment using the transformant, and an agent for the prophylaxis or treatment of rheumatoid arthritis which contains the antibody or antibody fragment.

10 Claims, 15 Drawing Sheets

FIG. 6
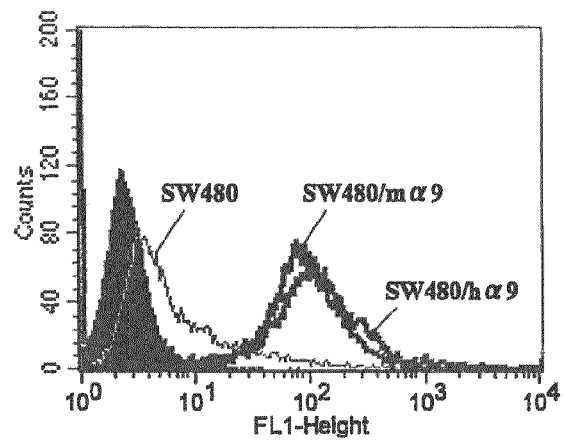
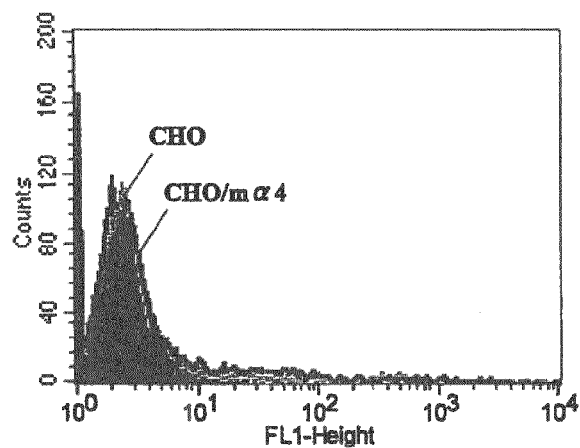

FIG. 7
a) 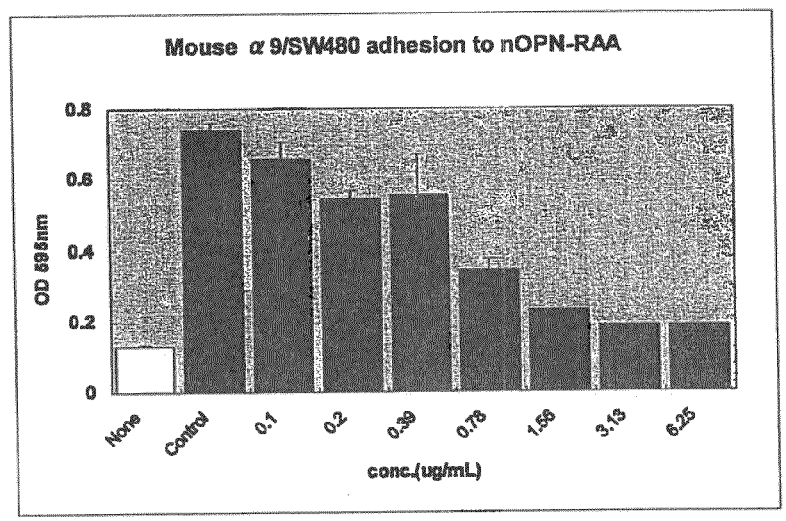
b) 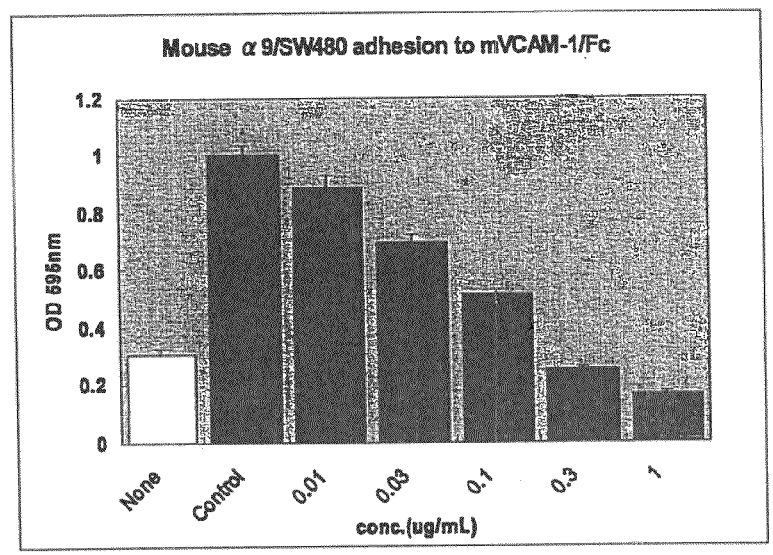
c) 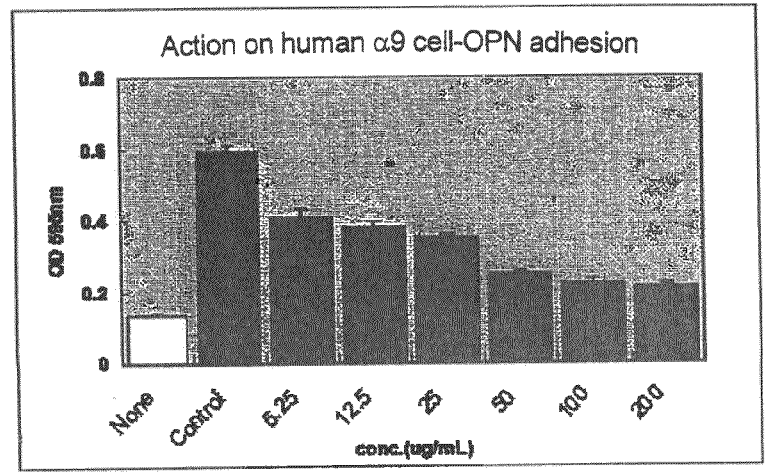

FIG. 8

```
                                                                        R1
human a4-propeller    1 YNVDTESALLYQGPHNTLFGYSVVLHSHGANRWLLVGAH TANWLANASVINH GAIYRCRI   60
human a9-propeller    1 FNLDAERPVHFQGPADSFFGYAVLEHFHDNTRWVLVGAH KADSKYSPSVKSH GAVFKCRV   60
mouse a9-propeller    1 YNLDAQRPVRFQGPSGSFFGYAVLEHFHDNTRWVLVGAH KADSKYSTSVKSH GAVFKCRV   60
                        .*.*.....  .***   ..***.*..*.*...**.*****.*......**..***...**.
                                         L1
human a4-propeller   61 GKNPGQTCEQLQLG SP--NGEPCGKTCLEERDN QWLGVTLSRQPGENGSIVTQ GHRWKNI  118
human a9-propeller   61 HTNPDRRCTELDMH RGKNRGTSCGKTCREDRDD EWMGVSLARQPKADGRVLAQ AHRWKNI  120
mouse a9-propeller   61 HTNPDRRCTELDMH RGRTRGAPCGKTCRGDRDD EWMGVSLARQPRADGRVLAQ AHRWKNI  120
                        ..**...*..*.*....  .*  .*****...**..*.**.*.***  .*..*..******.
                        R2                                R3a
human a4-propeller  119 FYIKNENKLPTGG CYGVPPDLRTELSKRIAPQ YQDYVKKFGENFAS CQAGISSFYTKDLI  178
human a9-propeller  121 YYEADHI-LPHGH CYIIPSNLQAKGRTLI-PQ YEEYKKKYGEEHGS CQAGIAGFFTEELV  178
mouse a9-propeller  121 YYEADHI-LPHGH CYLIPSNLQAKGKVLI-PQ YEEYKKKYGEEHGS CQAGIAGFFTEELV  178
                        .*.....  **.*.**  .*..*.*....   .* ***.**..**.**...*****..**..**.
                        R3b    R3c                                  L2
human a4-propeller  179 VMQAPGS SYWTGS LFVYNITTNKYKAFLDKQNQ V-K-FGSYLGYSVG AGHFRSQHTTEVV  236
human a9-propeller  179 VMQAPGS FYWAGT LKVLNLTDNTYLKLNDEVI-MNRRYT-YLGYAVT AGHFSHPSTIDVV  236
mouse a9-propeller  179 VMQAPGS FYWAGT LKVLNLTDNTYFKLNDEAI-MNRRYT-YLGYAVT AGHFSHPSITDVV  236
                        ******.**   **..*..*.*.*.*   ...*.  .  ....   ****.*.****.......**
                        R4                       L3            R5
human a4-propeller  237 GGAPQHEQIGR AYIFSIDEKE--LNI-IHEMKGKKLGSYFGASV CAVI LNADGFS DLLVG  293
human a9-propeller  237 GGAPQDKGIGR VYIFRADRRSGTLIKIPQ-ASGKKMGSYFGSSI CAVD LNGDGLS DLLVG  295
mouse a9-propeller  237 GGAPQDEGIGR VYIFRADRRSGTLVKIPQ-ASGKKMGSYFGSSI CAVD LNMDGLS DLLVG  295
                        *****...***.***..*......*  ....  ..***.*****.*.******  **.******
                        L4
human a4-propeller  294 APMQSTIREEGR VFVYINSGSGAVMNAMETNLVGSDKYAARFGESIVNLGDIDNDGFEDV  353
human a9-propeller  296 APMFSEIRDEGQ VTVYINRGNGALEEQLA--LTGDGAYNAHFGESIASLDDLDNDGFPDV  353
mouse a9-propeller  296 APMFSEIRDEGQ VTVYINQGHGALEEQLT--LTGDAAYNAHFGESIANLGDIDDDGFPDV  353
                        ***.*.**.**.**.**.*.**.*  *   **.....  *.*.  .*.*.*****..*.*.*.***.**

human a4-propeller  354 AIGAPQEDDLQGAIYIYNGRADGISSTFSQRIEGLQISKSLSMFGQSISGQIDADNNGYV  413
human a9-propeller  354 AIGAPKEDDFAGAVYIYHGDAGGIVPQYSMKLSGQKINPVLRMFGQSISGGIDMDGNGYP  413
mouse a9-propeller  354 AVGAPKEEDFAGAVYIYHGDANGIVPKYSMKLSGRRLNPTLRMFGQSISGGIDMDGNGYP  413
                        *.***.*..**..**.***.*.*   **.. .*....*    ...*.********.**.*.***.

human a4-propeller  414 DVAVGAFRSDSAVLLRT  430
human a9-propeller  414 DVTVGAFMSDSVVLLRA  430
mouse a9-propeller  414 DVTIGAFLSDSVVLLRA  430
                        **..***.***.****.
```

FIG. 13
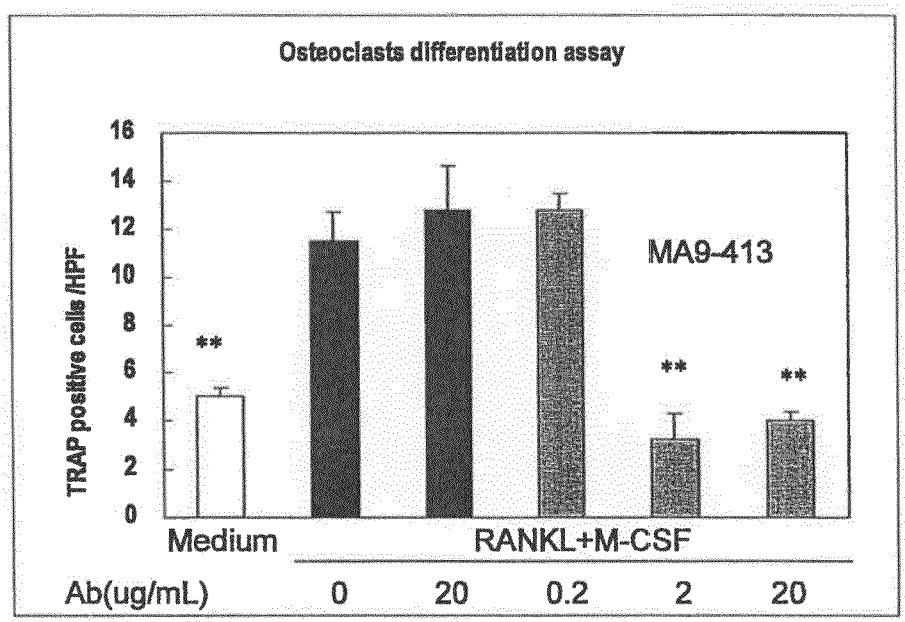
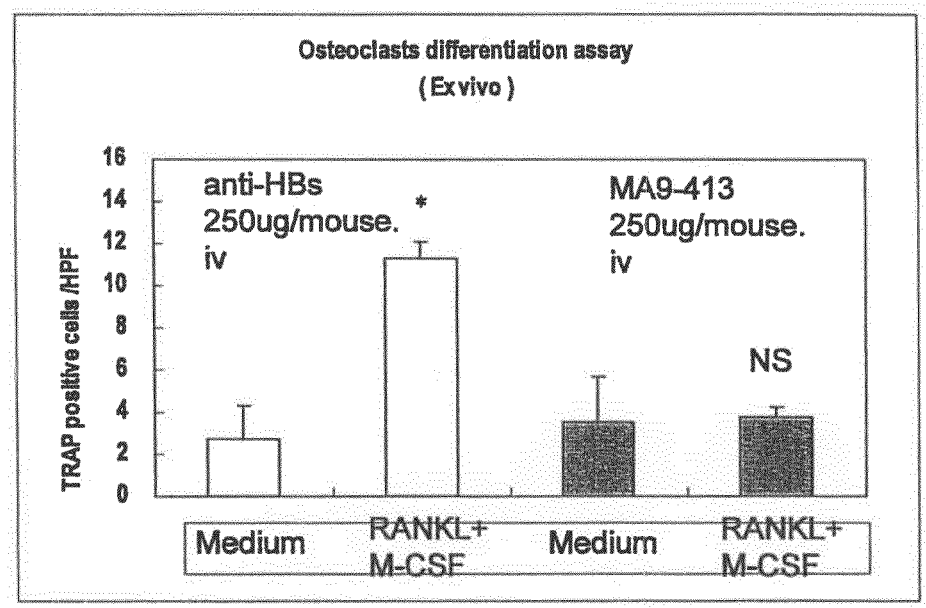

FIG. 14

VH
```
              10          20          30          40          50          60          70
MA9-413   EVQLVESGGG  VVRPGGSLRL  SCAASGFAFG  DYGMSWVRQA  PGKGLEWVSG  INWNGGSTGY  ADSVKGRFTT
MA9-418   ----------  ----------  ----------  ----------  ----------  ----------  ----------
HA9-107   ----------  ----------  ----------  ----------  ----------  ----------  ----------
HA9-143   ----------  ----------  ----------  E---------  ----------  ----------  ----------
HA9-212   ----------  ----------  ----------  E---------  ----------  ----------  ---Q------

80          90         100         110         120
MA9-413   SRDNAKNSLY  LQMNSLRAED  TALYYCARDE  NYDILTGYYY  YGMDVWGQGT  TVTVSS
MA9-418   ----------  ----------  ----------  ---A------  ----------  ------
HA9-107   ----------  ----------  ----------  ---NE-----  ----------  ------
HA9-143   ----------  ----------  ----------  ---H------  ----------  ------
HA9-212   ----------  ----------  ----------  ---N------  ----------  ------
```

VL
```
              10          20          30          40          50          60          70
MA9-413   QSVVTQPPSV  SAAPGQKVTI  SCSGSSSNIG  NNYVSWYQQL  PGTAPKLLIY  DNNKRPSGIP  DRFSASKSGT
MA9-418   ----------  ----------  ----------  ----------  ----------  ----------  ----------
HA9-107   ----------  ----------  ----------  ----------  ----------  ----------  ----------
HA9-143   ----------  ----------  ----------  ----------  ----------  ----------  ----------
HA9-212   ----------  ----------  ----------  ----------  ----------  ----------  ----------

80          90         100         110
MA9-413   SATLGITGLQ  TGDEADYYCG  TWDSSLTVWA  FGGGTKLTVL  G
MA9-418   ----------  ----------  ----------  ----------  -
HA9-107   ----------  ----------  ----------  ----------  -
HA9-143   ----------  ----------  ----------  ----------  -
HA9-212   ----------  ----------  ----------  ----------  -
```

HUMAN ANTI-α9 INTEGRIN ANTIBODY

The present application is a 35 U.S.C. §371 National Stage patent application of International patent application PCT/JP2008/073825, filed on Dec. 26, 2008, which claims priority to Japanese patent application JP 2007-340203, filed on Dec. 28, 2007.

TECHNICAL FIELD

The present invention relates to a human anti-α9 integrin antibody and an application thereof. Specifically, the present invention relates to a human anti-α9 integrin antibody that binds to a loop region of human and mouse α9 integrin protein designated as L1 to inhibit α9 integrin-dependent cell adhesion, and to exhibit suppressive action on arthritis, and a fragment of the antibody, as well as to the diagnosis, prevention or treatment of autoimmune diseases such as rheumatoid arthritis, immune diseases such as allergies and graft rejections, and other various diseases involved by α9 integrin in their pathogenesis, using the antibody or antibody fragment.

BACKGROUND ART

Integrin, a cell surface glycoprotein, is an adhesion molecule that functions mainly as a receptor for cell adhesion to extracellular matrices (collagen, laminin and the like) and members of the immunoglobulin family (ICAM-1, VCAM-1 and the like), and mediates signal transduction from extracellular matrices. Thereby, cells receive signals from the extracellular matrices, and differentiation, proliferation, cell death and the like are induced. Integrin is a heterodimer consisting of the two subunits α chain and β chain; there are different α chains and β chains occurring in a wide variety of combinations, and there are 24 members of the integrin superfamily. Integrin-knockout mice are fatal or diseased irrespective of which subunit is lacked, suggesting that individual integrins are necessary for the maintenance of life. Therefore, integrin, which transmits information on ambient conditions to cells to stimulate their responses, are thought to function in all situations of biological phenomena, and to mediate a broad range of pathologic conditions.

As such, integrin is indispensable to the survival of organisms, and is thought to play roles even in diseased states; some cases have been reported in which their inhibition helps improve pathologic conditions. For example, an inhibitor of platelet-specific integrin αIIbβ3 has been approved as a therapeutic drug for PCTA restenosis known as abciximab (trade name: ReoPro; Eli Lilly). Natalizumab (trade name: Antegren; ELAN Company), an α4β1 (VLA4) inhibitor, has been approved as a therapeutic drug for multiple sclerosis. The αvβ3 inhibitor Vitaxin (MEDIMMUNE Company) is under development in clinical studies for its neovascularization inhibitory action, osteoclast activation inhibitory action and the like.

Integrin α9β1 is expressed in macrophages, NKT cells, dendritic cells, and neutrophils, and reportedly plays important roles in the infiltration and adhesion of these inflammatory cells, bone resorption and the like. Recently, it has been reported that integrin α9β1 is involved in osteoclast formation, and its involvement in bone destruction has been suggested (Non-patent Document 1). Known ligands thereof include truncated osteopontin (N-terminal OPN), VCAM-1, Tenascin-C and the like. Clinically, significantly elevated levels of integrin α9β1 have been observed in the synovial tissues of patients with rheumatoid arthritis (Non-patent Document 2).

Therefore, a monoclonal antibody that binds specifically to α9 integrin protein to act to inhibit α9 integrin-dependent cell adhesion, if developed, would be useful in the diagnosis, prevention or treatment of various diseases involved by α9 integrin in their pathogenesis.

Antibodies that have been reported to exhibit function inhibitory action on human α9 integrin are the mouse monoclonal antibody Y9A2 (Non-patent Document 3), and 1K11, 24I11, 21C5 and 25B6, which are also mouse monoclonal antibodies (Patent Document 1). Although in vitro experimental results have shown that these antibodies are capable of suppressing human α9 integrin-dependent cell adhesion, they are unsuited for use in experiments for in vivo evaluations of pharmacological effects and the like because they do not exhibit cross-reactivity to mouse and rat α9 integrin.

Antibodies that have been reported to exhibit function inhibitory action on mouse α9 integrin are the hamster monoclonal antibodies 11L2B, 12C4'58, 18R18D and 55A2C (Patent Document 1). In vitro experimental results have shown that these antibodies are capable of suppressing functions of mouse α9, such as cell adhesion, and in vivo experimental results have shown that 11L2B has a therapeutic effect on hepatitis; however, their reactivity to human α9 integrin has not been confirmed, so it is impossible to apply these antibodies to the treatment or prevention of human diseases.

As the situation stands, even if an anti-human α9 integrin antibody is acquired and functionally evaluated in vitro, it is difficult to evaluate the pharmacological effect of the antibody unless it exhibits cross-reactivity to mouse or rat α9 integrin, because the available pathologic models of various inflammatory diseases are for the most part systems using a mouse or rat. Even if an anti-mouse α9 integrin antibody is acquired and pharmacologically evaluated using an in vivo pathologic model system, and is found to be therapeutically or prophylactically effective, it is impossible to apply the antibody as an antibody pharmaceutical to human pathologic conditions unless it exhibits cross-reactivity to human α9 integrin.

Provided that an anti-human α9 monoclonal antibody such as Y9A2 is developed as an antibody pharmaceutical on the basis of pharmacological effect data obtained using an anti-mouse α9 integrin antibody, a great deal of labor will be required to demonstrate equivalence of the antibody used to acquire the pharmacological data and the antibody under development. For this reason, there is a demand for, for example, an antibody that exhibits inhibitory action on function of both mouse α9 integrin and human α9 integrin; judging from the principles, however, it is difficult to acquire such an antibody when using a conventional method such as one involving mouse immunization.

Even if an anti-human α9 monoclonal antibody prepared by any technique overcoming this difficulty is developed as an antibody pharmaceutical, the antibody will be recognized and eliminated as a foreign matter because of the high immunogenicity thereof when administered to humans, as far as the antibody is an antibody derived from non-human animal. Therefore, it is difficult to use such an antibody as a therapeutic drug for a disease.

As a possible solution to this problem, a non-human-derived antibody may be humanized using a protein engineering technique; however, because a portion of the non-human-derived sequence is contained, multiple-dose administration or long-term administration can give rise to an antibody that inhibits the activity of the humanized anti-α9 integrin antibody administered to considerably weaken the effect thereof, and even can cause a serious adverse reaction. Additionally, humanization often results in decreased activity, and a humanized antibody requires a great deal of labor and cost for its construction.

As the situation stands for α9 integrin, there is almost no structural information on the steric structure, ligand binding site, neutralizing epitope and the like; such information, if obtained, is expected to open a way to research into α9 integrin and its application to medical practice, and potentially makes a great contribution.

Patent Document 1: WO 2006/075784
Non-patent Document 1: Journal of Bone and Mineral Research, 2006, 21: 1657-1665
Non-patent Document 2: The Journal of Clinical Investigation, 2005, 115: 1060-1067
Non-patent Document 3: Am. J. Respir. Cell Mol. Biol., 1996, 15: 664-672

DISCLOSURE OF THE INVENTION

Problems to be Solved by the Invention

Accordingly, it is an object of the present invention to provide a human anti-α9 integrin antibody that exhibits specific reactivity to both human α9 integrin and mouse α9 integrin, and reconciles safety and therapeutic efficacy, and to provide a novel prophylactic or therapeutic means for various diseases involved by α9 integrin in their pathogenesis, by means of the potent anti-inflammatory action and bone destruction suppressive action of the human anti-α9 integrin antibody based on the blockage of the interaction between α9 integrin and a plurality of ligands thereof.

Means for Solving the Problems

The present inventors succeeded in preparing a human anti-α9 integrin antibody and antibody fragment that exhibit specific reactivity to mouse α9 integrin and human α9 integrin by preparing an α9 integrin-expressing cell, and reacting the cell directly with an antibody phage library on which a human antibody has been displayed. Furthermore, the inventors found that the antibody and antibody fragment inhibit α9 integrin-dependent cell adhesion, exhibit a therapeutic effect on a plurality of arthritis models, and suppress the differentiation of osteoclasts in the models. Hence, the inventors demonstrated that the antibody and antibody fragment reconcile safety and therapeutic efficacy, and have developed the present invention.

Accordingly, the present invention encompasses the following aspects 1) to 16) as medically or industrially useful methods and substances.

1) A human anti-α9 integrin antibody or antibody fragment that recognizes human α9 integrin and mouse α9 integrin and inhibits the interaction between the α9 integrins and ligands.
2) The antibody or antibody fragment described in 1) above, that recognizes an epitope configured mainly by the region from the 104th Arg to the 122nd Asp of human α9 integrin (SEQ ID NO:36), and an epitope configured mainly by the region from the 105th Arg to the 123rd Asp of mouse α9 integrin (SEQ ID NO:37).
3) The antibody or antibody fragment described in 1) or 2) above, that has (a) heavy-chain complementarity determining regions and (b) light-chain complementarity determining regions (CDR1, CDR2, CDR3), which regions consist of the amino acid sequences shown by the following sequence identification numbers, respectively.

(a) Heavy-chain complementarity determining regions CDR1, CDR2, CDR3
SEQ ID NO:2, SEQ ID NO:3, SEQ ID NO:4;
SEQ ID NO:13, SEQ ID NO:14, SEQ ID NO:15;
SEQ ID NO:19, SEQ ID NO:20, SEQ ID NO:21;
SEQ ID NO:25, SEQ ID NO:26, SEQ ID NO:27; or
SEQ ID NO:31, SEQ ID NO:32, SEQ ID NO:33;
(b) light-chain complementarity determining regions CDR1, CDR2, CDR3
SEQ ID NO:7, SEQ ID NO:8, SEQ ID NO:9
4) The antibody or antibody fragment described in 3) above, that has heavy-chain complementarity determining regions CDR1, CDR2, CDR3, which regions consist of the amino acid sequences shown by SEQ ID NO:31, SEQ ID NO:32, and SEQ ID NO:33, respectively.
5) The antibody or antibody fragment described in 1) or 2) above, that has a heavy-chain variable region consisting of the amino acid sequence shown by any one of SEQ ID NO:1, SEQ ID NO:12, SEQ ID NO:18, SEQ ID NO:24, and SEQ ID NO:30, and a light-chain variable region consisting of the amino acid sequence shown by SEQ ID NO:6.
6) The antibody or antibody fragment described in 5) above, that has a heavy-chain variable region consisting of the amino acid sequence shown by SEQ ID NO:30.
7) The human anti-α9 integrin antibody described in any one of 1) to 6) above, wherein the antibody is a complete antibody.
8) The human anti-α9 integrin antibody fragment described in any one of 1) to 6) above, wherein the antibody fragment is scFv or scFv-Fc.
9) A gene that encodes the antibody or antibody fragment described in any one of 1) to 8) above.
10) A recombinant expression vector comprising the gene described in 9) above.
11) A transformant incorporating the gene described in 9) above.
12) A method of producing a human anti-α9 integrin antibody or antibody fragment by allowing the gene described in 9) above to be expressed in a host.
13) A prophylactic or therapeutic agent for rheumatoid arthritis comprising the antibody or antibody fragment described in any one of 1) to 8) above.
14) A method of preventing or treating rheumatoid arthritis in a subject, comprising the step of administering a therapeutically effective amount of the antibody or antibody fragment described in any one of 1) to 8) above to the subject.
15) A use of the antibody or antibody fragment described in any one of 1) to 8) above in producing a prophylactic or therapeutic agent for rheumatoid arthritis.
16) The antibody or antibody fragment described in any one of 1) to 8) above for preventing or treating rheumatoid arthritis.

Effect of the Invention

The human monoclonal antibody of the present invention and the antibody fragment thereof have a variable region of human-derived anti-α9 integrin antibody, and possess specific reactivity to human and mouse α9 integrin, inhibitory activity against α9 integrin-dependent cell adhesion, and suppressive action on arthritis. The epitope thereof was found to be a loop region that has not been reported in any other integrin families (designated as L1). Because the antibody and antibody fragment according to the present invention are complete human antibodies, they are expected to find new applications as diagnostic, prophylactic or therapeutic drugs for various diseases involved by α9 integrin.

BRIEF DESCRIPTION OF THE DRAWINGS

FIG. 6 is a graphic representation showing results of an analysis of the reactivity and specificity of MA9-413 scFv-Fc to mouse α9 and human α9 by flowcytometry.

FIG. 7 is a graphic representation showing the inhibitory potential of MA9-413 scFv-Fc against mouse α9- and human α9-dependent cell adhesion.

FIG. 8 is an illustration showing the amino acid sequences of the β propeller domains of α9 and loop regions estimated by modeling. FIG. 8 discloses SEQ ID NOS: 38-40, respectively, in order of appearance. Specifically, SEQ ID NO: 38 corresponds to the sequence identified as "human a4-propeller"; SEQ ID NO: 39 corresponds to the sequence identified as "human a9-propeller"; and SEQ ID NO: 40 corresponds to the sequence identified as "mouse a9-propeller."

FIG. 13 is a graphic representation showing the osteoclast differentiation suppression by MA9-413 scFv-Fc in mouse collagen antibody-induced arthritis.

FIG. 14 is an illustration showing the amino acid sequences of altered MA9-413. FIG. 14 discloses SEQ ID NOS: 1, 12, 18, 24, 30, 6, 6, 6, 6, and 6, respectively, in order of appearance. Specifically, the respective amino acid sequences in FIG. 14 are shown in SEQ ID NO:1 (VH:MA9-413), SEQ ID NO:12 (VH:MA9-418), SEQ ID NO:18 (VH:HA9-107), SEQ ID NO:24 (VH:HA9-143), SEQ ID NO:30 (VH:HA9-212) and SEQ ID NO:6 (VL).

BEST MODE FOR CARRYING OUT THE INVENTION

Figure 1:
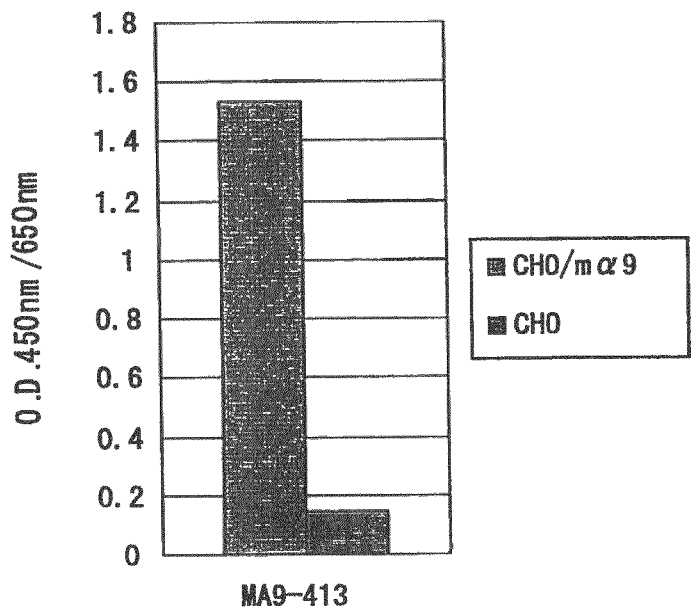
FIG. 1 is a graphic representation showing the reactivity of an scFv display phage to mouse α9.

The present invention is hereinafter described in detail.

An scFv display phage library can be prepared as described below. Immunoglobulin heavy (H) chain and light (L) chain cDNAs are synthesized by an RT-PCR method from peripheral blood B lymphocytes collected from a plurality of healthy volunteers. Next, by amplifying the H chain variable regions (VHs) and L chain variable regions (VLs) with the use of a combination of various primers, and binding both with linker DNA, a library of scFv genes based on a random combination of VHs and VLs derived from lymphocytes from the healthy volunteers is prepared. This scFv gene can be integrated in a phagemid vector (e.g., pCANTAB5E) to construct an scFv display phage library consisting of about $10^8$ to $10^{11}$ clones from the healthy volunteers.

Preparation of α9 integrin, which is an antigen, can be performed as described below.

Because α9 integrin (hereinafter, also simply referred to as "α9") is a membrane protein, it is possible to clone the α9 gene and transfect a cultured cell therewith to artificially express the gene on the surface of the cultured cell. It is recommended that a cDNA library or the like be used as a template for the gene cloning. To express the gene on the cell surface, a signal sequence must usually be present in the N-terminal portion; therefore, the signal sequence intrinsically possessed by α9 may be utilized, and a gene region that encodes mature α9 may be joined with another signal sequence. Regarding the antibody prepared, it is necessary to evaluate the species specificity and the like to assess the applicability and potential of the antibody, so it is desirable that the gene be acquired for both human α9 and mouse α9.

The thus-acquired α9 gene, which comprises a signal sequence, is cloned into an expression vector, for example, the pcDNA3.1(-) vector (Invitrogen) and the like. Here, of the α chains of the integrin family, α4 is said to be most highly homologous to α9. For this reason, desirably, it is recommended that α4 integrin, for use as a control for α9, be subjected to the same operation and cloned into the expression vector.

The expression vector constructed is transferred to a cultured cell such as a CHO cell or SW480 cell by transfection using Lipofectamine 2000 (Invitrogen) and the like. Expressing cells can be selected by means of an expression vector marker (neomycin and the like), and the cells thus obtained can be used for subsequent screening and evaluations. For the expressing cells, it is recommended that cells that exhibit high expression more stably be obtained by performing cloning such as by limiting dilution to yield a homogeneous cell population.

Described below is how to prepare an antibody. When it is intended to prepare an anti-α9 integrin antibody and conduct target validation of α9, it is recommended that a monoclonal antibody possessing function inhibitory activity be first acquired with mouse α9 as a target, and then the antibody is examined for the presence or absence of a pharmacological effect using a mouse pathologic model system.

First, separation of a specific clone from an scFv display phage library is described. For example, this can be achieved by the procedures shown below. After the foregoing library is reacted with CHO cells and subtraction is performed, it is bound to mouse α9-expressing CHO cells, recovered and concentrated, and an anti-α9 scFv display phage clone is screened for. The antigen used may not be the cell as it is, but a membrane fraction may be prepared and used, or an antigen may be purified from a membrane fraction and used.

An scFv of the clone thus obtained is prepared, and its reactivity to α9-expressing cells is checked. As a method scFv expression, the scFv can be expressed in, for example, *Escherichia coli*. In case of *Escherichia coli*, the scFv can be expressed in a state functionally bound with a useful promoter in common use, a signal sequence for antibody secretion and the like. As examples of the promoters, the lacZ promoter, araB promoter and the like can be mentioned. As a signal sequence for scFv secretion, it is recommended that the pelB signal sequence (J. Bacterio. R1987, 169: 4379-4383) be used when the scFv is to be expressed in *Escherichia coli* periplasm. For secretion in the culture supernatant, the signal sequence of the M13 phage g3 protein can also be used.

The scFv expressed outside the cell can be separated from the host and purified to homogeneity. For example, the scFv expressed using the pCANTAB5E system can be purified easily in a short time by affinity chromatography using an anti-Etag antibody because it has an Etag sequence added to the C-terminus thereof. In addition, the scFv can also be purified using a combination of methods of protein separation and purification in common use. For example, by combining ultrafiltration, salting-out, and column chromatographies such as gel filtration/ion exchange/hydrophobic chromatography, the antibody can be separated and purified. The purified product may be analyzed for molecular form by HPLC gel filtration analysis and the like.

As methods of measuring the binding activity of the antibody or antibody fragment obtained for α9 integrin, ELISA, FACS and the like are available. When using ELISA, for example, a sample containing the desired antibody or antibody fragment, for example, an *Escherichia coli* culture supernatant or purified antibody, is added to a 96-well plate on which α9 integrin-expressing cells have been immobilized directly or via a capture antibody. Next, a secondary antibody such as an anti-Etag antibody, previously labeled with an enzyme such as horseradish peroxidase (HRP) or alkaline phosphatase (AP), a fluorescent substance such as fluorescein isocyanate or rhodamine, a radioactive substance such as $^{32}P$ or $^{125}I$, a chemiluminescent substance or the like, is added and reacted, and the plate is washed, after which a detection reagent (in case of HRP labeling, for example, color developing substrate TMB and the like) is added as required, and the absorbance, fluorescence intensity, radioactivity, the amount of luminescence and the like is measured, whereby antigen the binding activity can be evaluated.

The DNA base sequences of the VH and VL of the scFv genes of the clone isolated can be determined by the dideoxy method and the like, and their amino acid sequences can be estimated from the DNA base sequence information obtained.

Furthermore, as a method of determining whether the separated clone possesses function inhibitory activity against α9, the following method with α9-dependent cell adhesion as an index, for example, is available. The RAA-altered form (the RGD sequence replaced with RAA to suppress the reaction with other integrins) of an N-terminal OPN (an N-terminal fragment resulting from truncation of osteopontin with thrombin), which is a ligand of α9, is immobilized on a plate, and blocking is performed. After various antibodies are added, α9-expressing cells are added, and incubated at 37° C. for 1 hour. After the cells are fixed and stained using Crystal violet and methanol, and washed, the dye in the adhering cells is extracted with Triton X-100, and its absorbance at a wavelength of 595 nm is determined. If suppressive action is confirmed thereby, the antibody is judged to possess inhibitory activity against α9.

Here, scFv is a monovalent antibody fragment; it is known that there are some cases in which the affinity or inhibitory effect is largely improved by an avidity effect when the scFv is replaced with an IgG-type or scFv-Fc-type divalent antibody. Another well-known fact is that molecular forms of relatively large molecular weights, such as the IgG type or scFv-Fc type, have better stability in the body and longer half-life than those of molecular forms of relatively small molecular weights, such as scFv.

For this reason, it is recommended that, for example, the separated clone be converted to the molecular form of the scFv-Fc type and evaluated as described below. The scFv gene region of the separated clone is amplified by PCR, and inserted into a mouse or human Fc fusion protein expression vector, whereby an scFv-Fc expression vector is constructed. As an example of such a mouse or human Fc fusion protein expression vector, pFUSE-mIgG1-Fc or pFUSE-hIgG1-Fc (InvivoGen Company) is usable. In the vector, a leader sequence that promotes extracellular secretory expression, the scFv gene, and the mouse or human Fc gene region have been joined, and the expression thereof is controlled by various promoters.

The constructed scFv-Fc expression vector is transfected to a cultured cell such as a CHO cell using Lipofectamine 2000 (Invitrogen) and the like. It is possible to perform expansion culture using a selection medium containing an expression vector marker (neomycin and the like), recover the culture supernatant, and purify it by Protein A column chromatography and the like. It is recommended that the purified reference standard of scFv-Fc obtained, like scFv, be analyzed by HPLC gel filtration, ELISA, FACS, or α9-dependent cell adhesion inhibition test and the like. In ELISA, detection can be performed using an HRP-labeled anti-mouse IgG antibody and the like; in FACS, detection can be performed using an FITC-labeled anti-mouse IgG antibody and the like. It is recommended that Y9A2 (CHEMICON), a mouse monoclonal antibody against human α9, be used as a control antibody.

Next, epitope analysis of antibody is described.

If an epitope of an antibody clone possessing function inhibitory activity is identified, it will be possible to clarify a neutralizing epitope of α9. Epitope analysis can be performed, for example, as described below. An α9 amino acid-substituted form is constructed, and the reactivity to the antibody is analyzed. If a change in the reactivity to the antibody due to the amino acid substitution is revealed, it is strongly suggested that the substituted site may be an epitope of the antibody. As examples of methods of amino acid substitution, exchanging the human α9 and mouse α9 sequences, exchanging the α9 and α4 sequences, replacing the α9 sequence with Ala, and the like are available.

Since the β propeller domain located at the N-terminal moiety of an extracellular region is reportedly the site of interaction with the ligand, which is a feature common to the α chains of the integrin family (Science, 296, 151-155, 2002), it seems likely that a neutralizing epitope is present in this region. Therefore, the β propeller domain may be the subject of analysis.

A reference document analyzing the ligand-binding site and neutralizing epitope of α4 (Proc. Natl. Acad. Sci. USA, 94, 7198-7203, 1997) presents results showing that R2 and R4, out of the repeat moieties called R1 to R5 in the β propeller domain (corresponding to the loop region), are important to ligand binding, and that R2, R3a and R3c can become neutralizing epitopes. Judging from these facts, it seems likely that the loop region is a neutralizing epitope. Therefore, the analysis may be performed while narrowing the coverage of targets to loop regions in the β propeller domain.

If available from the results of finished analysis, data on the specificity of the antibody may be utilized. For example, if a difference is observed in the strength of reactivity to human α9 and mouse α9, it is thought that the amino acid sequence of the epitope region may differ to some extent between humans and mice. Because human α9 and mouse α9 are highly homologous to each other, the coverage of candidate sites can be further narrowed to enable efficient analysis, provided that a site whose amino acid sequence differs between human α9 and mouse α9 is selected from among candidate sites to be analyzed.

It is also recommended that a fluorescent protein such as EGFP be used as a marker for confirming the expression of an altered human α9. For example, provided that an α9-EGFP conjugate with EGFP fused to the C terminus (cytoplasmic region) of α9 is constructed, the expression of α9 can be confirmed by fluorescence, and the reactivity of the antibody in proportion to the amount expressed can be evaluated, so a more quantitative evaluation is possible.

Such an amino acid-substituted form of α9 or α9-EGFP conjugate is constructed by site-directed mutagenesis and the like. They are cloned into an expression vector, and each is transferred to a cultured cell such as a CHO cell. For a transiently expressed or stably expressed cell population, the expression of wild-type or altered-type α9 (or α9-EGFP) and the reactivity thereof to the antibody can be evaluated using ELISA or FACS and the like. For example, when various amino acid-substituted forms are constructed on the basis of α9-EGFP, and their reactivities to the antibody are analyzed by FACS, the reactivities to the antibody per unit amount expressed can be discussed on in terms of the expression of α9-EGFP indicated on the lateral axis, and the reactivity to the antibody indicated on the vertical axis.

If the analysis reveals a change in the reactivity to the antibody due to an α9 amino acid substitution, the substituted site can be estimated to be an epitope of the antibody (or a portion of the epitope).

Next, an evaluation of the pharmacological effect of an antibody is described.

Since it has been strongly suggested that α9 may be involved in inflammation, it is recommended that mouse collagen antibody-induced arthritis, which is a representative model of arthritis, or the like be used as a mouse pathologic model system. For example, the pharmacological effect of each antibody clone on mouse collagen antibody-induced arthritis can be evaluated by the procedures shown below.

An anti-collagen antibody cocktail is administered to mice, and 3 days later, LPS is administered, whereby the onset of arthritis is induced. On the day of LPS administration and 3 days later, the scFv-Fc of the clone is intraperitoneally administered at 500, 170, and 56 μg/head. The degree of swelling in all limbs of each mouse is examined and scored over time, and changes over time in the mean value for each group are graphed. As a result, if an scFv-Fc dose-dependent suppressive effect on arthritis is observed, the clone is judged to have a pharmacological effect on arthritis.

Alternatively, it is recommended that the suppressive effect on mouse collagen-induced arthritis, which is another representative model of arthritis, be evaluated. It is known that in collagen antibody-induced arthritis, an inflammatory reaction in the acute stage is elicited, whereas in collagen-induced arthritis, a chronic inflammatory response mediated by an immune reaction is caused. For example, the pharmacological effect of the clone on mouse collagen-induced arthritis can be evaluated by the procedures shown below.

By administering bovine type II collagen to mice twice at a 3-week interval, the onset of arthritis is induced. 4 days, 6 days, 8 days, 10 days and 12 days after the second administration, the scFv-Fc of the clone is intraperitoneally administered at 500, 170, and 56 μg/head. The degree of swelling in all limbs of each mouse is examined and scored over time to determine whether an scFv-Fc dose-dependent suppressive effect on arthritis is observed.

Rheumatoid arthritis is a chronic inflammatory disease accompanied by joint destruction, and joint destruction deprives the patient of freedom, resulting in a major deterioration of his or her QOL. None of the rheumatoid arthritis therapeutic agents that have been used to date effectively suppress joint destruction, although they possess anti-inflammatory action; it is hoped that an rheumatoid arthritis therapeutic agent having both potent anti-inflammatory action and joint destruction suppressive action will be developed. Therefore, for example, the suppressive effect of the clone on osteoclast differentiation may be evaluated as described below.

Bone marrow cells are collected from the above-described artificially arthritic mouse, and cultured in an αMEM medium containing RANKL and M-CSF, along with the clone's scFv-Fc, after which osteoclasts (TRAP-positive cells) are counted, and the suppressive effect on differentiation into osteoclasts is evaluated. In another method, the scFv-Fc is administered simultaneously with induction of arthritis, bone marrow cells are collected from the mouse the following day, the cells are cultured in an αMEM medium containing RANKL and M-CSF, osteoclasts are counted, and the effect is evaluated.

Next, antibody affinity improvement is described.

Many cases have been reported in which alterations such as amino acid substitutions are performed on the variable region of an antibody, whereby the affinity or specificity was improved or changed. Even if the antibody obtained does not possess sufficient affinity or specificity, it seems possible to improve the affinity or specificity of the antibody, for example, as described below.

As methods of alterations, there are various methods commonly known in the art; for example, there are a method wherein a specified site is substituted with a particular amino acid such as Ala (for example, Current Protocols in Molecular Biology edit. 1987, 5: Section 8, 1-8), a method wherein random amino acids are introduced (both can be performed by site-directed mutagenesis), a method wherein amino acid substitutions are randomly introduced to the variable region of the antibody without specifying a site (can be performed by random mutagenesis) (e.g., PCR methods and Applications, 1992, 2: 28-33) and the like.

In many cases, of the various antibody variable regions, the CDR3 region of VH is the greatest contributor to antigen recognition, so this region may be the subject site for alteration.

It is also possible to prepare an altered scFv display phage library, and screen for an altered clone with improved affinity or specificity compared with the original clone.

Regarding the altered clone acquired, it is recommended that a reference standard be prepared in the molecular form of, for example, scFv or scFv-Fc, as with the original clone, and its reactivity, function inhibitory activity, and pharmacological effect, be evaluated. As a result, if a better property than the original clone, reactivity to human α9, and a pharmacological effect are confirmed, the altered clone is highly expected to become a prophylactic or therapeutic drug for a disease in which α9 contributes to the pathogenesis.

The present inventors attempted to acquire anti-α9 integrin scFv by the above-described method and, as a result, succeeded in acquiring MA9-413, an scFv clone possessing specific reactivity to α9 integrin. As a result of an evaluation after changing the molecular form from scFv to scFv-Fc, this clone was confirmed as having a property that has never been reported to date in that it exhibits reactivity to both human α9 and mouse α9 and function inhibitory activity against both.

Furthermore, the present inventors conducted epitope analysis on clone MA9-413, and found that this clone recognizes an epitope configured mainly by the region from the 104th Arg to the 122nd Asp of human α9 integrin (SEQ ID NO:36: a human α9 integrin shown by Swiss-Prot AC: Q13797; the N-terminus of the amino acid sequence is numbered 1), and an epitope configured mainly by the region from the 105th Arg to the 123rd Asp of mouse α9 integrin (SEQ ID NO:37: a mouse α9 integrin shown by GenBank ACCESSION: AJ344342; the N-terminus of the amino acid sequence is numbered 1). These regions are loop regions whose functions and roles have not been reported in past studies of other integrin families, and the present inventors designated them as L1 regions.

As a result of an examination of the pharmacological effects of the antibody and antibody fragment having these characteristics, an effect to significantly suppress inflammation and joint swelling in a mouse arthritis model was confirmed.

Hence, the human anti-α9 integrin antibody and antibody fragment of the present invention have a property that has not been reported to date in that they recognize an epitope formed by the L1 region of α9 integrin and possess reactivity to both mouse α9 integrin and human α9 integrin. As such, the antibody and antibody fragment of the present invention are expected to be industrially applicable as novel diagnostic, prophylactic or therapeutic drugs for various diseases involved by α9 integrin.

Because the human anti-α9 integrin antibody and antibody fragment of the present invention possess reactivity to both mouse α9 integrin and human α9 integrin, it is possible to acquire data on pharmacological studies using mice with the same antibody and further conduct clinical studies in human subjects to promote the development of an antibody pharmaceutical, as stated above; this can be said to be a major advantage in view of industrial application.

The present invention also offers a new potential for investigational or industrial applications concerning α9 integrin and even the integrin family as a whole, as a result of the finding of a novel neutralizing epitope called the L1 region.

Furthermore, the present inventors made molecular alterations to the foregoing clone MA9-413, and succeeded in obtaining a plurality of clones with remarkably improved reactivity to human α9 integrin: MA9-418, HA9-107, HA9-143 and HA9-212. These clones are expected to become more effective drugs than MA9-413.

The amino acid sequences of the VH chains and VL chains of the scFv clones acquired by the present inventors, which have the above-described properties, and the base sequences that encode them are shown below.

(1) Clone MA9-413

The amino acid sequence of the VH chain of clone MA9-413 is shown by SEQ ID NO:1. The amino acid sequences of the CDR1 to 3 of the VH chain are shown by SEQ ID NO:2 to 4. Hence, in the amino acid sequence of the VH chain shown by SEQ ID NO:1, the sequence of the 31st to 35th amino acids corresponds to the CDR1 (SEQ ID NO:2), the sequence of the 50th to 66th amino acids corresponds to the CDR2 (SEQ ID NO:3), and the sequence of the 99th to 115th amino acids corresponds to the CDR3 (SEQ ID NO:4). The base sequence of the gene that encodes the VH chain is shown by SEQ ID NO:5.

The amino acid sequence of the VL chain of clone MA9-413 is shown by SEQ ID NO:6. The amino acid sequences of the CDR1 to 3 of the VL chain are shown by SEQ ID NO:7 to 9. Hence, in the amino acid sequence of the VL chain shown by SEQ ID NO:6, the sequence of the 23rd to 35th amino acids corresponds to the CDR1 (SEQ ID NO:7), the sequence of the 51st to 57th amino acids corresponds to the CDR2 (SEQ ID NO:8), and the sequence of the 90th to 96th amino acids corresponds to the CDR3 (SEQ ID NO:9). The base sequence of the gene that encodes the VL chain is shown by SEQ ID NO:10.

(2) Clone MA9-418

The amino acid sequence of the VH chain of clone MA9-418 is shown by SEQ ID NO:12. The amino acid sequences of the CDR1 to 3 of the VH chain are shown by SEQ ID NO:13 to 15. Hence, in the amino acid sequence of the VH chain shown by SEQ ID NO:12, the sequence of the 31st to 35th amino acids corresponds to the CDR1 (SEQ ID NO:13), the sequence of the 50th to 66th amino acids corresponds to the CDR2 (SEQ ID NO:14), and the sequence of the 99th to 115th amino acids corresponds to the CDR3 (SEQ ID NO:15). The base sequence of the gene that encodes the VH chain is shown by SEQ ID NO:16.

The amino acid sequence of the VL chain of clone MA9-418 is the same as that of the VL chain of clone MA9-413 (SEQ ID NO:6).

(3) Clone HA9-107

The amino acid sequence of the VH chain of clone MA9-107 is shown by SEQ ID NO:18. The amino acid sequences of the CDR1 to 3 of the VH chain are shown by SEQ ID NO:19 to 21. Hence, in the amino acid sequence of the VH chain shown by SEQ ID NO:18, the sequence of the 31st to 35th amino acids corresponds to the CDR1 (SEQ ID NO:19), the sequence of the 50th to 66th amino acids corresponds to the CDR2 (SEQ ID NO:20), and the sequence of the 99th to 115th amino acids corresponds to the CDR3 (SEQ ID NO:21). The base sequence of the gene that encodes the VH chain is shown by SEQ ID NO:22.

The amino acid sequence of the VL chain clone MA9-107 is the same as that of the VL chain of clone MA9-413 (SEQ ID NO:6).

(4) Clone HA9-143

The amino acid sequence of the VH chain of clone HA9-143 is shown by SEQ ID NO:24. The amino acid sequences of the CDR1 to 3 of the VH chain are shown by SEQ ID NO:25 to 27. Hence, in the amino acid sequence of the VH chain shown by SEQ ID NO:24, the sequence of the 31st to 35th amino acids corresponds to the CDR1 (SEQ ID NO:25), the sequence of the 50th to 66th amino acids corresponds to the CDR2 (SEQ ID NO:26), and the sequence of the 99th to 115th amino acids corresponds to the CDR3 (SEQ ID NO:27). The base sequence of the gene that encodes the VH chain is shown by SEQ ID NO:28.

The amino acid sequence of the VL chain of clone HA9-143 is the same as that of the VL chain of clone MA9-413 (SEQ ID NO:6).

(5) Clone HA9-212

The amino acid sequence of the VH chain of clone HA9-212 is shown by SEQ ID NO:30. The amino acid sequences of the CDR1 to 3 of the VH chain are shown by SEQ ID NO:31 to 33. Hence, in the amino acid sequence of the VH chain shown by SEQ ID NO:30, the sequence of the 31st to 35th amino acids corresponds to the CDR1 (SEQ ID NO:31), the sequence of the 50th to 66th amino acids corresponds to the CDR2 (SEQ ID NO:32), and the sequence of the 99th to 115th amino acids corresponds to the CDR3 (SEQ ID NO:33). The base sequence of the gene that encodes the VH chain is shown by SEQ ID NO:34.

The amino acid sequence of the VL chain of clone HA9-212 is the same as that of the VL chain of clone MA9-413 (SEQ ID NO:6).

In a preferred embodiment, the human anti-α9 integrin antibody or antibody fragment of the present invention has heavy-chain complementarity determining regions consisting of the amino acid sequences shown by SEQ ID NO:2, SEQ ID NO:3, SEQ ID NO:4; SEQ ID NO:13, SEQ ID NO:14, SEQ ID NO:15; SEQ ID NO:19, SEQ ID NO:20, SEQ ID NO:21; SEQ ID NO:25, SEQ ID NO:26, SEQ ID NO:27; or SEQ ID NO:31, SEQ ID NO:32, and SEQ ID NO:33, respectively (CDR1, CDR2, CDR3), and light-chain complementarity determining regions consisting of the amino acid sequences shown by SEQ ID NO:7, SEQ ID NO:8, and SEQ ID NO:9, respectively (CDR1, CDR2, CDR3). In a more preferred embodiment, the human anti-α9 integrin antibody or antibody fragment has heavy-chain complementarity determining regions consisting of the amino acid sequences shown by SEQ ID NO:31, SEQ ID NO:32, and SEQ ID NO:33, respectively (CDR1, CDR2, CDR3).

In a still more preferred embodiment, the human anti-α9 integrin antibody or antibody fragment of the present invention has a heavy-chain variable region (VH) consisting of the amino acid sequence shown by any one of SEQ ID NO:1, SEQ ID NO:12, SEQ ID NO:18, SEQ ID NO:24, and SEQ ID NO:30, and a light-chain variable region (VL) consisting of the amino acid sequence shown by SEQ ID NO:6. In a most preferred embodiment, the human anti-α9 integrin antibody or antibody fragment has a heavy-chain variable region (VH) consisting of the amino acid sequence shown by SEQ ID NO:30.

The VH chains and/or VL chains disclosed in the present invention have been obtained in the form of scFv using the phage antibody method, and they were evaluated in the molecular form of scFv or scFv-Fc; as a rule, however, the human anti-α9 integrin antibody or antibody fragment of the present invention is not limited to these molecular forms. For example, a complete molecular form prepared by joining a disclosed VH chain and/or VL chain to the constant region of human immunoglobulin, as a complete antibody, and not only scFv and scFv-Fc, but also Fab, Fab' or F(ab')$_2$ combined with a portion of the constant region of human immunoglobulin, and other antibody fragments such as single-stranded antibodies prepared by binding scFv to the constant region of the L chain of human immunoglobulin (scAb), as antibody fragments, are also encompassed in the present invention.

In addition to the above-described anti-human α9 integrin antibody of the present invention or antibody fragment thereof, the present invention also encompasses fusion antibodies prepared by fusing the antibody or antibody fragment with another peptide or protein, and modified antibodies prepared by binding the antibody or antibody fragment with a polymeric modifier such as polyethylene glycol.

In preparing an scFv with the Fvs of an H chain and L chain joined via an appropriate linker, for example, an optionally chosen single-stranded peptide consisting of 10 to 25 amino acid residues, is used as a peptide linker.

The human anti-α9 integrin antibody or an antibody fragment, a fused antibody resulting from fusion of said antibody or antibody fragment with another peptide or protein, or a modified antibody consisting of said antibody or antibody fragment and a modifying agent bound thereto (hereinafter to be referred to as "human anti-α9 integrin antibody etc.") of the present invention thus obtained, after being further purified as required, can be prepared as a pharmaceutical preparation according to a conventional method, and can be used for the prophylaxis and/or treatment of autoimmune diseases such as rheumatoid arthritis, immune diseases such as allergy, graft rejection etc., or diseases wherein α9 integrin is involved in pathogenesis such as osteoarthritis, chronic obstructive pulmonary disease, cancer and the like.

The human anti-α9 integrin antibody etc. of the present invention can be used preferably as a therapeutic agent for rheumatoid arthritis. As examples of dosage forms for such therapeutic agent, a parenteral preparation such as an injection or drip infusion can be prepared, and is preferably administered by intravenous administration, subcutaneous administration and the like (the same applies in the case of an autoimmune disease therapeutic agent). In preparing a pharmaceutical preparation, carriers and additives that match these dosage forms can be used within a pharmaceutically acceptable range.

The amount of human anti-α9 integrin antibody etc. added in the above-described preparation making varies depending on the patient symptom severity and age, the dosage form of the preparation used or the binding titer of the antibody and the like; for example, about 0.1 mg/kg to 100 mg/kg may be used.

The present invention also provides a gene that encodes the antibody of the present invention or a fragment thereof, and an expression vector comprising the same. The expression vector of the present invention is not subject to limitation, as long as it is capable of expressing a gene that encodes the antibody of the present invention or a fragment thereof in various host cells of prokaryotic cells and/or eukaryotic cells, and producing these polypeptides. For example, plasmid vectors, viral vectors (for example, adenovirus, retrovirus) and the like can be mentioned.

The expression vector of the present invention can comprise a gene that encodes the antibody of the present invention or a fragment thereof, and a promoter functionally joined to the gene. As the promoter for expressing the polypeptide of the present invention in a bacterium, when the host is a bacterium of the genus *Escherichia*, for example, the Trp promoter, lac promoter, recA promoter, λPL promoter, 1pp promoter, tac promoter and the like can be mentioned. As the promoter for expressing the antibody of the present invention or a fragment thereof in yeast, for example, the PH05 promoter, PGK promoter, GAP promoter, and ADH promoter can be mentioned; when the host is a bacterium of the genus *Bacillus*, the SL01 promoter, SP02 promoter, penP promoter and the like can be mentioned. When the host is a eukaryotic cell such as a mammalian cell, CAG promoter (Niwa H. et al., Gene, 108, 193-200, 1991), SV40-derived promoter, retrovirus promoter, heat shock promoter and the like can be mentioned.

When a bacterium, particularly *Escherichia coli*, is used as the host cell, the expression vector of the present invention can further comprise an initiation codon, a stop codon, a terminator region and a replicable unit. When a yeast, animal cell or insect cell is used as the host, the expression vector of the present invention can comprise an initiation codon and a stop codon. In this case, an enhancer sequence, noncoding regions on the 5' side and 3' side of a gene that encodes the polypeptide of the present invention, a splicing junction, a polyadenylation site, or a replicable unit and the like may be contained. A selection marker in common use (for example, tetracycline, ampicillin, kanamycin) may be contained according to the intended use.

The present invention also provides a transformant incorporating the gene of the present invention. Such a transformant can be prepared by, for example, transforming a host cell with the expression vector of the present invention. The host cell used to prepare a transformant is not subject to limitation, as long as it matches the aforementioned expression vector, and is transformable; various cells such as natural cells or artificially established lines of cells in common use in the technical field of the present invention (for example, bacteria (bacteria of the genus *Escherichia*, bacteria of the genus *Bacillus*), yeasts (the genus *Saccharomyces*, the genus *Pichia* and the like), animal cells or insect cells (for example, Sf9 and the like) can be mentioned as examples. The transformation can be performed by a method known per se.

The present invention also provides a method of producing the antibody of the present invention or a fragment thereof, comprising allowing a host cell to express the gene of the present invention, i.e., using such a transformant.

In producing the antibody of the present invention or a fragment thereof, the transformant can be cultured in nutrient medium. The nutrient medium preferably contains a carbon source and an inorganic nitrogen source or organic nitrogen source required for the growth of the transformant. As examples of the carbon source, glucose, dextran, soluble starch, sucrose and the like can be mentioned; as examples of the inorganic nitrogen source or organic nitrogen source, ammonium salts, nitrates, amino acids, corn steep liquor, peptone, casein, meat extract, soybean cake, potato extract and the like can be mentioned. If desired, other nutrients (for example, inorganic salts (for example, calcium chloride, sodium dihydrogen phosphate, magnesium chloride), vitamins, antibiotics (for example, tetracycline, neomycin, ampicillin, kanamycin and the like) and the like) may be contained.

Cultivation of the transformant can be performed by a method known per se. Cultivation conditions, for example, temperature, pH of the medium, and cultivation time are selected as appropriate. For example, when the host is an animal cell, an MEM medium containing about 5 to 20% fetal bovine serum (Science, Vol. 122, p. 501, 1952), DMEM medium (Virology, Vol. 8, p. 396, 1959), RPMI1640 medium (J. Am. Med. Assoc., Vol. 199, p. 519, 1967), 199 medium (Proc. Soc. Exp. Biol. Med., Vol. 73, p. 1, 1950) and the like can be used as the medium. The pH of the medium is preferably about 6 to 8, cultivation is normally performed at about 30 to 40° C. for about 15 to 72 hours, and the culture may be aerated or agitated as necessary. When the host is an insect cell, for example, Grace's medium comprising fetal bovine serum (Proc. Natl. Acad. Sci. USA, Vol. 82, p. 8404, 1985) and the like can be mentioned, and the pH thereof is preferably about 5 to 8. Cultivation is normally performed at about 20 to 40° C. for 15 to 100 hours, and the culture may be aerated or agitated as necessary. When the host is a bacterium, an actinomyces, yeast, or a filamentous fungus, for example, a liquid medium comprising the above-described nutrient sources is appropriate. A medium having a pH of 5 to 8 is preferable. When the host is *E. coli*, LB medium, M9 medium (Miller et al., Exp. Mol. Genet, Cold Spring Harbor Laboratory, p. 431, 1972) and the like can be mentioned as preferable media. In this case, cultivation can be normally performed at 14 to 43° C. for about 3 to 24 hours, while aerating or agitating the culture as necessary. When the host is a bacterium of the genus *Bacillus*, cultivation can be normally performed at 30 to 40° C. for about 16 to 96 hours, while aerating or agitating the culture as necessary. When the host is yeast, Burkholder's minimal medium (Bostian, Proc. Natl. Acad. Sci. USA, Vol. 77, p. 4505, 1980) can be mentioned as examples of the medium, and the pH is desirably 5 to 8. Cultivation is normally performed at about 20 to 35° C. for about 14 to 144 hours, and the culture may be aerated or agitated as necessary.

The antibody of the present invention or a fragment thereof can be recovered, preferably isolated and purified, from a cultured transformant as described above. As examples of the method of isolation and purification, methods based on differences in solubility, such as salting-out and solvent precipitation; methods based on differences in molecular weight, such as dialysis, ultrafiltration, gel filtration, and sodium dodecyl sulfate-polyacrylamide gel electrophoresis; methods based on differences in electric charge, such as ion exchange chromatography and hydroxyl apatite chromatography; methods based on specific affinity, such as affinity chromatography; methods based on differences in hydrophobicity, such as reverse phase high performance liquid chromatography; methods based on differences in isoelectric point, such as isoelectric focusing; and the like can be mentioned.

The present invention is explained in detail in the following based on Examples, which are not to be construed as limitative.

EXAMPLES

Example 1

Preparation of Antigen

Using human cDNA library as a template, the major domain region of human α9 integrin gene and the signal sequence region of human α5 integrin gene were cloned. The signal sequence region of human α5 integrin gene and the major domain region of human α9 integrin gene were connected and incorporated into pcDNA3.1(−) vector (Invitrogen) to construct a human α9 expression vector.

Using mouse cDNA library as a template, the full-length mouse α9 integrin gene was cloned and incorporated into pcDNA3.1(+) vector (Invitrogen) to construct a mouse α9 expression vector.

In addition, for use as a control, human α4 integrin and mouse α4 integrin were also cloned according to the following procedure.

Using human cDNA library as a template, the full-length human α4 integrin gene was cloned and incorporated into pcDNA3.1(+) vector (Invitrogen) to construct a human α4 expression vector.

Using mouse spleen-derived cDNA as a template, the full-length mouse α4 integrin gene was cloned and incorporated into pcDNA3.1(+) vector (Invitrogen) to construct a mouse α4 expression vector.

Firstly, the mouse α9 integrin expression vector and the mouse α4 integrin expression vector were respectively introduced into CHO cells, and a mouse α9 integrin-expressing cell (hereinafter to be referred to as CHO/mα9) and a mouse α4 integrin-expressing cell (hereinafter to be referred to as CHO/mα4) were respectively established.

Then, the human α9 integrin expression vector and the mouse α9 integrin expression vector were respectively introduced into SW480 cells, and a human α9 integrin-expressing cell (hereinafter to be referred to as SW480/hα9) and a mouse α9 integrin-expressing cell (hereinafter to be referred as SW480/mα9) were respectively established.

These various integrin-expressing cells were used for the following screening and evaluation.

Example 2

Construction of Phage Library From Healthy Volunteers

By reference to the method reported by J. D. Marks et al. (J. Mol. Biol., 222: 581-597, 1991) and using lymphocytes derived from peripheral blood of twenty healthy volunteers as a starting material, a phage library was constructed. The constructed sublibraries VH(γ)-Vκ, VH(γ)-Vλ, VH(μ)-Vκ and VH(μ)-Vλ were assessed to have diversity of $1.1 \times 10^8$, $2.1 \times 10^8$, $8.4 \times 10^7$ and $5.3 \times 10^7$ clones, respectively.

Example 3

Screening Using α9 Integrin-Expressing Cell

A specific antibody to α9 was produced according to the following procedures. First, a monoclonal antibody having a function inhibitory activity was constructed with mouse α9 as a target, and the presence or absence of efficacy was evaluated using a mouse pathology model system.

Using the parental strain CHO cell, phage display library was subtracted, and reacted with CHO/mα9. The reaction was performed for 1 hr, and the cells were washed 3 times with 1% BSA/PBS.

The cell fraction after washing was suspended in HCl (10 mM), and incubated for 10 min to elute phage. The eluate was neutralized by mixing with 1M Tris-HCl (pH 7.5), and infected with TG1 to amplify phage.

As a result of 4 rounds of panning, a phage clone MA9-413 specifically reactive with mouse α9 was isolated.

Example 4

Analysis of Reactivity of Phage Antibody by ELISA

The reactivity of MA9-413 phage antibody to α9 was analyzed by Cell ELISA.

CHO/mα9 and CHO were seeded on a 96 well plate (costar) at $2 \times 10^4$ cells/100 µL/well, and incubated overnight at 37° C., 5% $CO_2$. The medium was suctioned, and the cells were washed with PBS, and reacted with phage antibody diluted with 1% BSA/PBS. The detection was performed by using horse-radish peroxidase (HRP)-labeled anti-M13 antibody (Amersham) and TMB (SIGMA) in combination. The absorbance at wavelengths 450 nm and 650 nm was measured by a microplate reader (Molecular Devices). The results are shown in FIG. 1. Since α9-specific reactivity of MA9-413 was confirmed, subsequent analyses were performed.

Example 5

Sequence Analysis of Clone

The DNA base sequences of VH and VL of scFv gene of isolated clone were determined by using a CEQ DTCS Quick Start Kit (BECKMAN COULTER). The amino acid sequence was deduced based on the information of the obtained DNA base sequences.

Example 6

Expression and Purification of scFv

Plasmid DNA was recovered from specific clone MA9-413, and *Escherichia coli* JM83 was transformed according to a conventional method. The *Escherichia coli* was precultured overnight in 2×YT medium containing 2% glucose and 100 µg/mL ampicillin, and partly transferred into SB medium containing 2% glucose and 100 µg/mL ampicillin to perform the main culture. IPTG was added in the logarithmic phase to a final concentration of 1 mM, and the mixture was cultured for 3 hr to induce scFv expression. After completion of the culture, bacterial cells were recovered by centrifugation, suspended in 100 mM Tris-HCl solution (pH 7.4) containing 20% sucrose and 10 mM EDTA and the bacterial cells were stood still on ice for 30 min. Then, the cells were centrifuged at 8,900×g for 30 min, the supernatant was recovered, and the fraction obtained by filtration through 0.45 µm filter was taken as a periplasm fraction. Using the fraction as a starting material, scFv was purified according to a conventional method by SP column chromatography (Amersham) or RPAS Purification Module (Amersham), and the obtained elution fraction was dialyzed against PBS to give an scFv purification standard product.

Example 7

Analysis of Reactivity of scFv By ELISA

Figure 2:
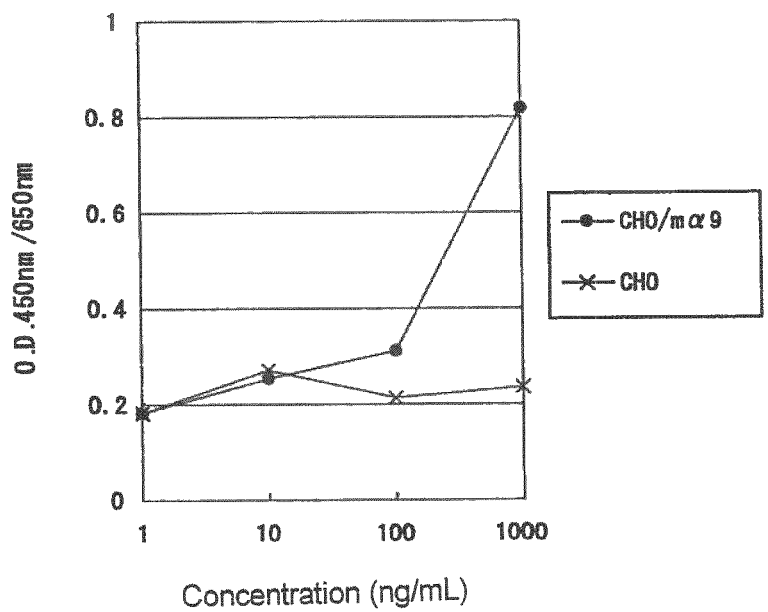
FIG. 2 is a graphic representation showing the reactivity of MA9-413 scFv to mouse α9.

The reactivity of the scFv purification product prepared in Example 6 to α9 was analyzed by Cell ELISA. For detection, an HRP-labeled anti-Etag antibody (Amersham) was used, and the rest was performed under the same conditions as in Example 4. As a result, a concentration-dependent and specific reactivity was confirmed as shown in FIG. 2.

Example 8

Assessment of α9-Dependent Cell Adhesion Inhibitory Activity of scFv

Whether MA9-413 scFv can inhibit α9-dependent cell adhesion was assessed by the following method.

N-terminal OPN variant (OPN variant with RGD sequence altered to RAA) was immobilized on a plate and subjected to blocking. MA9-413 scFv purification product was added, then SW480/mα9 was added, and the mixture was incubated at 37° C. for 1 hr. The cells were fixed and stained with Crystal violet and methanol, and washed. The dye in the adhered cells was extracted with Triton X-100, and the absorbance at wavelength 595 nm was measured.

Figure 3:
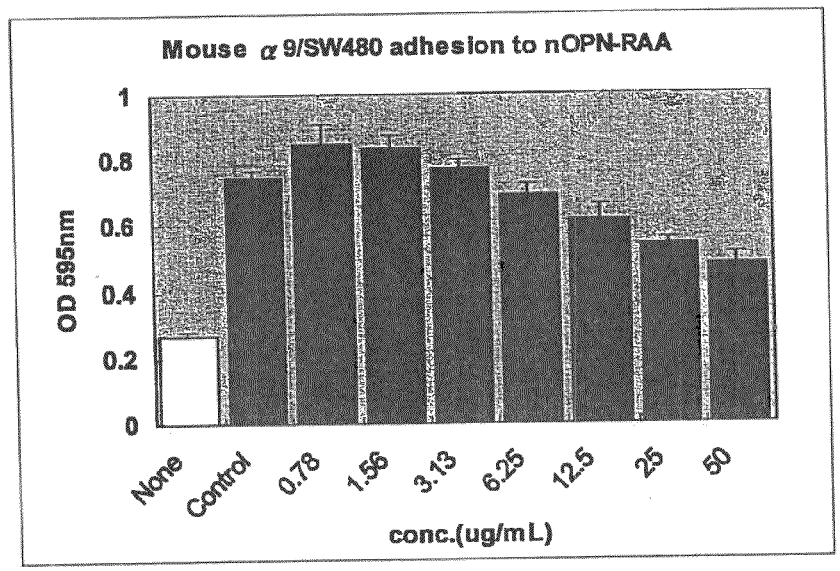
FIG. 3 is a graphic representation showing the inhibitory potential of MA9-413 scFv against mouse α9-dependent cell adhesion.

As a result, a concentration-dependent suppressive action was observed as shown in FIG. 3, and MA9-413 was confirmed to have a inhibitory activity against mouse α9.

Example 9

Construction of scFv-Fc Expression Vector

Figure 4:
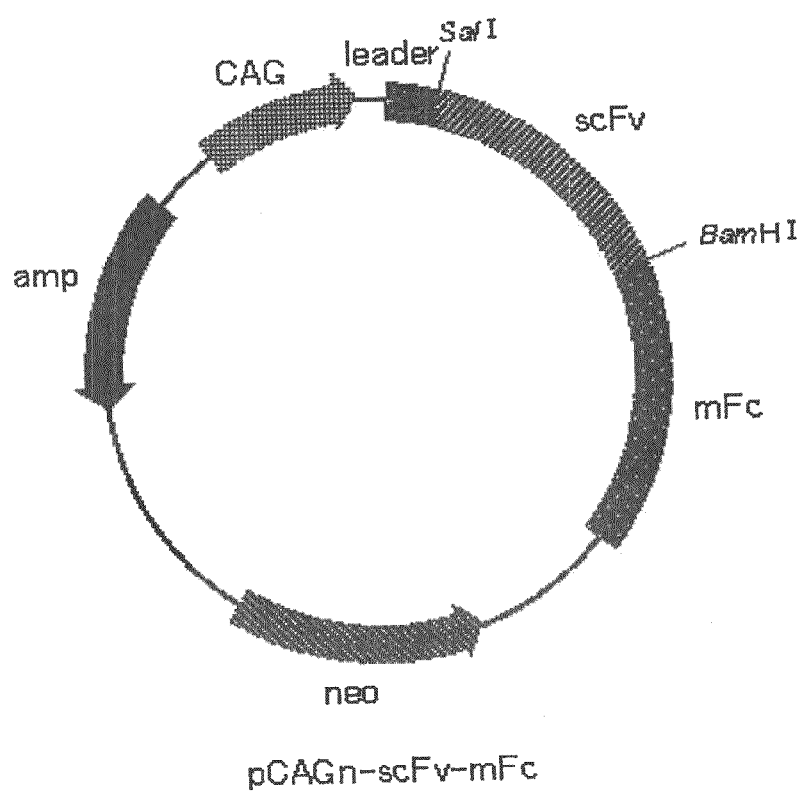
FIG. 4 is an illustration showing the structure of an scFv-Fc expression vector.

With the hope of improving the function inhibitory activity by changing the clone to a divalent antibody, the clone was converted to a molecular form of scFv-Fc. MA9-413 scFv gene region was amplified by PCR, and inserted into the SalI site and BamHI site of mouse Fc fusion protein expression vector to construct scFv-Fc expression vector shown in FIG. 4. In this vector, a leader sequence promoting extracellular secretory expression, scFv gene and a gene encoding the Fc region of mouse IgG1 are connected, and the expression thereof is regulated by CAG promoter. In addition, this vector contains a neomycin resistance gene and an ampicillin resistance gene as drug resistance genes.

Example 10

Expression and Purification of scFv-Fc

Using Lipofectamine 2000 (Invitrogen), the constructed scFv-Fc expression vector was transfected to CHO-DG44 strain. The cells were cultured in α-MEM medium (Invitrogen) or EXCELL302 medium (Nichirei Biosciences) containing 500 μg/mL neomycin and 10% bovine serum, and the culture supernatant was recovered. Affinity-purification was performed by Protein A column chromatography according to a conventional method and dialysis was performed with PBS. The obtained scFv-Fc solution was taken as the purified product.

Example 11

Analysis of Reactivity of scFv-Fc By ELISA

Figure 5:
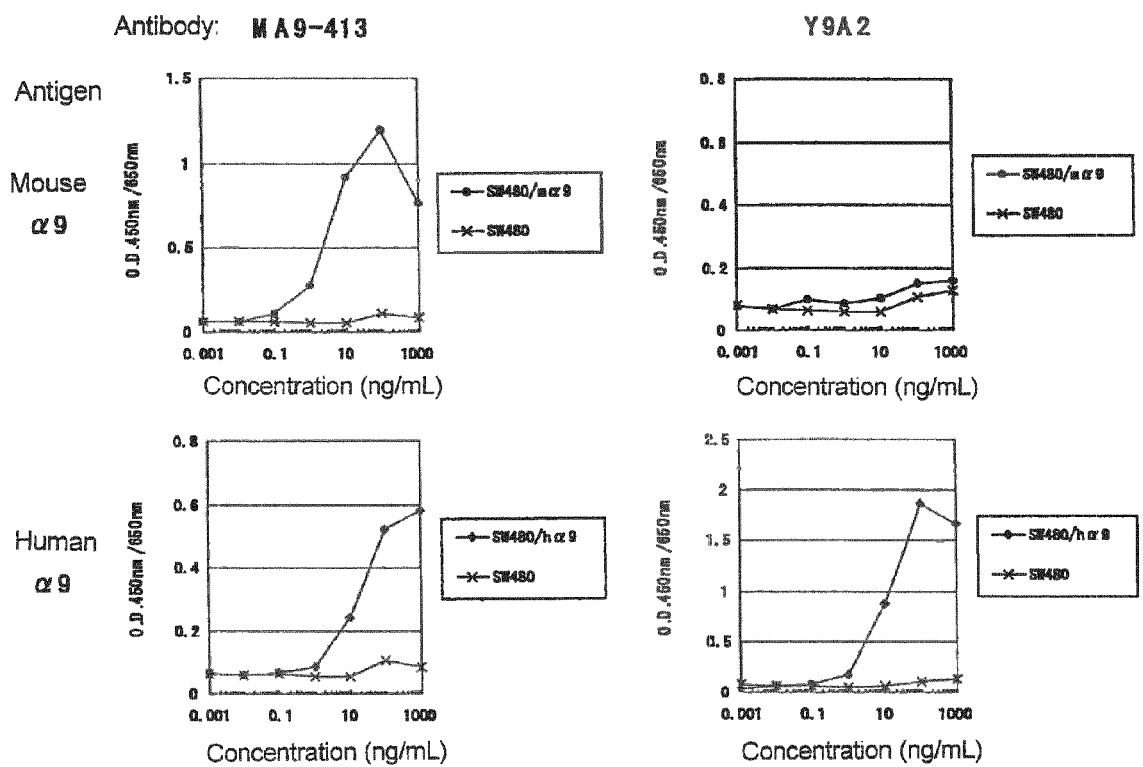
FIG. 5 is a graphic representation showing results of an analysis of the reactivity of MA9-413 scFv-Fc to mouse α9 and human α9 by ELISA.

The reactivity of MA9-413 scFv-Fc with mouse α9 and human α9 was analyzed by Cell ELISA. SW480/mα9, SW480/hα9 and SW480 were used as antigens, 1% BSA/PBS containing 5% FBS was used as a dilution solution, an HRP-labeled anti-mouse IgG antibody (ZYMED) was used for detection, and the rest was performed under the same conditions as in Example 4. As a result, a concentration-dependent and specific reactivity with mouse α9 and human α9 was observed as shown in FIG. 5. On the other hand, Y9A2 antibody assessed as a control reacted with human α9 but did not at all show any reactivity with mouse α9. From these results, it has been clarified that MA9-413 is an antibody clone having novel reactivity not reported before, which is capable of recognizing both mouse α9 and human α9.

Example 12

Analysis of Reactivity of scFv-Fc By Flow Cytometry

Furthermore, the reactivity of MA9-413 scFv-Fc was assessed by flow cytometry.

MA9-413 scFv-Fc was reacted with each of SW480, SW480/mα9 and SW480/hα9, and flow cytometry analysis was performed. As a result, the reactivity with mouse α9 and human α9 was confirmed. Although the reactivity with each of CHO and CHO/mα4 was also assessed in the same manner, the reactivity with mouse α4 was not observed (FIG. 6). From these results, it has been confirmed that MA9-413 scFv-Fc reacts with mouse and human α9 with high specificity.

Example 13

Assessment of α9-Dependent Cell Adhesion Inhibitory Activity of scFv-Fc

Whether MA9-413 scFv-Fc can inhibit mouse α9- and human α9-dependent cell adhesion was assessed.

As for cell adhesion when the ligand is OPN, SW480/mα9 or SW480/hα9 was used, and the rest was performed under the same conditions as in Example 8.

The cell adhesion when the ligand is VCAM-1 was assessed by the following method.

Mouse VCAM-1/Fc was immobilized on a plate and subjected to blocking. SW480/mα9 was used as the cell and the rest was performed under the same conditions as in Example 8.

As a result, a concentration-dependent suppressive action was observed in all cases as shown in FIG. 7, and it has been confirmed that MA9-413 has inhibitory activity against mouse α9 and human α9, and a similar action is observed even when the ligand is OPN or VCAM-1.

Example 14

Analysis of MA9-413 Epitope

MA9-413 having properties not reported before in that it shows reactivity with both mouse α9 and human α9 as well as inhibitory activity on the both was subjected to the following analysis in an attempt to identify epitope.

As a feature common to the integrin family α chains, β propeller domain present in the extracellular region N-terminal portion is said to be an interaction site with ligand (Science, 296, 151-155, 2002). Thus, a hypothesis was made that a neutralizing epitope is present in this region.

Then, by reference to the steric structural model of β propeller domain of human α4 reported in a publication (Proc. Natl. Acad. Sci. USA, 94, 65-72, 1997), a steric structural model of β propeller domain of human α9 was prepared. The β sheet region and loop region were deduced from the model (to be mentioned later).

In addition, a publication analyzing α4 ligand binding site and neutralizing epitope reports the results that, among the repeat sites (corresponding to loop region) referred to as R1 to R5 in the β propeller domain, R2 and R4 are important for ligand binding, and R2, R3a and R3c can be neutralizing epitopes (Proc. Natl. Acad. Sci. USA, 94, 7198-7203, 1997). Therefrom it has been considered that MA9-413 epitope is highly possibly a loop region.

To apply the finding obtained about α4 to α9, therefore, we aligned amino acid sequences of β propeller domains of human α4, human α9 and mouse α9 cloned by us, and compared the sequences (FIG. 8). The amino acid sequences of the respective β propeller domains of human α4, human α9 and mouse α9 shown in FIG. 8 are shown in SEQ ID NO: 38, SEQ ID NO: 39 and SEQ ID NO: 40. Among the loop regions deduced from the model, four regions not corresponding to R1 to R5 were named L1 to L4. The past study results suggest stronger reactivity of MA9-413 with mouse α9 than human α9, which suggests possible presence of a slight difference in the amino acid sequences of the epitope region between human and mouse. Therefore, the loop regions having different amino acid sequences between human α9 and mouse α9 were selected to give four regions of R1, R4, R5 and L1.

Then, based on human α9, amino acid in each of the above-mentioned four loop regions was substituted to construct a variant, and the reactivity with MA9-413 was assessed. First, EGFP was used as a marker for confirmation of the expression of human α9 variant, and a gene of human α9-EGFP fusion protein (hereinafter to be referred to as hα9-EGFP) wherein EGFP was fused with the C-terminal (cytoplasmic region) of human α9 was constructed. EGFP gene was amplified by PCR using a pEGFP-N1 vector (Clontech) as a template, and further connected to human α9 gene by assembly PCR. Utilizing restriction enzyme cleavage site, the gene was incorporated into the human α9 expression vector described in Example 1 to construct hα9-EGFP expression vector.

Using the above-mentioned human α9-EGFP fusion protein expression vector as a base, expression vectors of the four loop region variants were produced. For R1, a variant wherein the 47th Pro (following the numbering in FIG. 8, hereinafter the same) was substituted by Ala (hereinafter to be referred to as hα9/mR1-EGFP) was constructed, for R4, a variant wherein the 243rd Lys was substituted by Glu (hereinafter to be referred to as hα9/mR4-EGFP) was constructed, for R5, a variant wherein the 286th Gly was substituted by Ala (hereinafter to be referred to as hα9/mR5-EGFP) was constructed, and for L1, a variant wherein the 77th Lys was substituted by Arg, the 78th Asn was substituted by Thr, the 81st Thr was substituted by Ala, the 82nd Ser was substituted by Pro, and the 89th Glu was substituted by Gly (hereinafter to be referred to as hα9/mL1-EGFP) was constructed each by site-directed mutagenesis.

Furthermore, for confirmation of β propeller domain certainly being an epitope, a variant wherein the whole β propeller domain was substituted by human α4 β propeller domain (hereinafter to be referred to as hα4/9-EGFP) was constructed as follows. Since the region between restriction enzymes BlpI site and StuI site of human α9 gene exactly corresponds to the β propeller domain, human α4 gene region corresponding to the region was amplified by PCR using a primer appended with BlpI site and StuI site and human α4 expression vector as a template, cleaved with BlpI and StuI, and exchanged with the above-mentioned region between BlpI site and StuI site of the human α9-EGFP fusion protein expression vector.

The expression vectors of the above-mentioned wild-type and 5 kinds of variants were respectively introduced into CHO cells to give transiently expressed cell populations. Expression of the wild-type or variant α9-EGFP and reactivity with antibodies thereof were first assessed using FACScan (BECTON DICKINSON).

Figure 9:
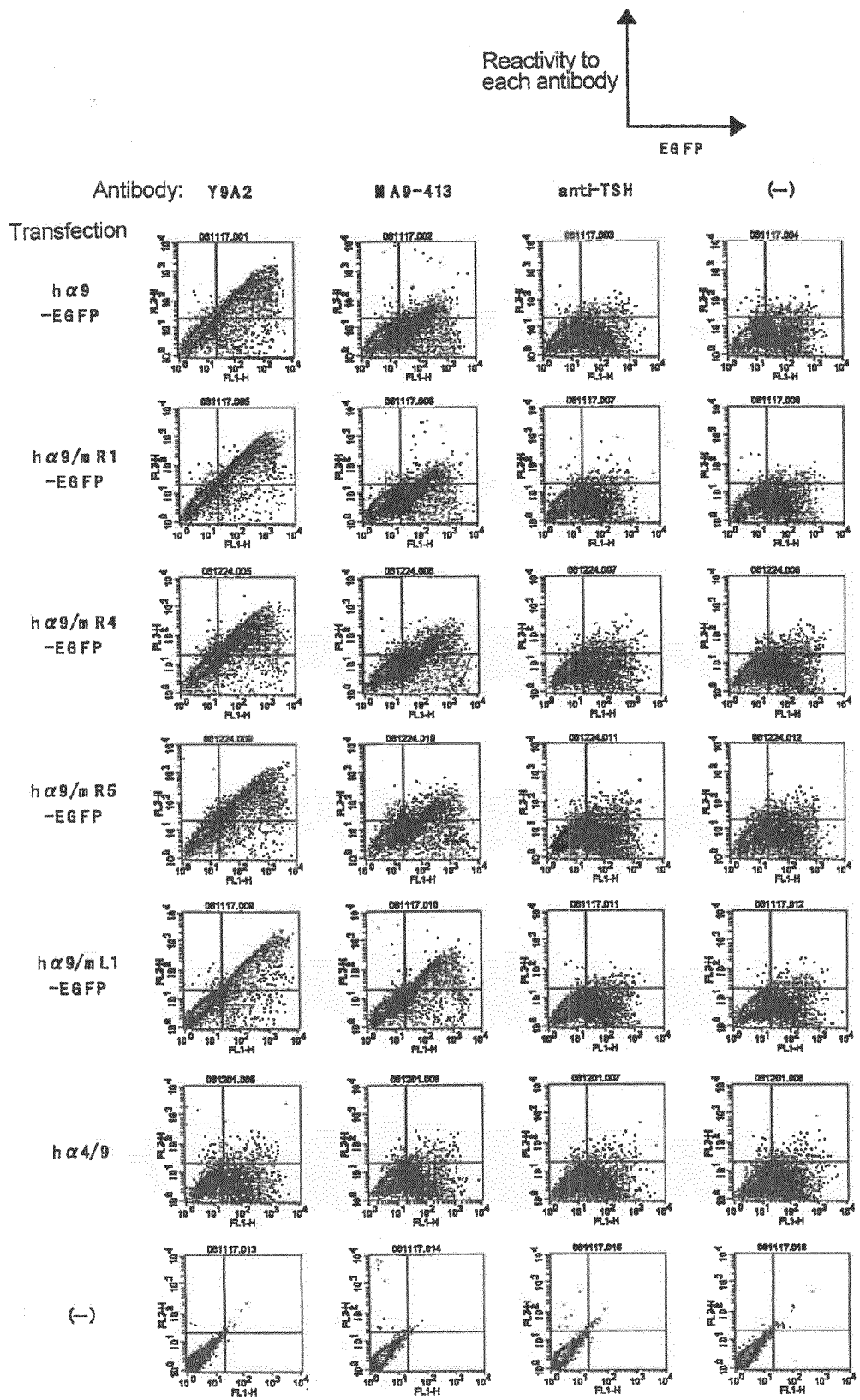
FIG. 9 is a graphic representation showing results of an analysis of the reactivity of MA9-413 scFv-Fc to altered α9 loop regions and altered α9 β propeller domains by flowcytometry.

Respective α9 expressing cell populations were reacted with control antibody or MA9-413 scFv-Fc diluted with 1% BSA/PBS containing 2% normal rabbit serum and 0.05% NaN$_3$ on ice for 30 min. After washing, the cell populations were reacted with PerCP-labeled anti-mouse IgG1 antibody (BECTON DICKINSON) on ice for 30 min, further washed, and analyze by FACScan. The results are shown in FIG. 9. The horizontal axis shows the expression of wild-type or variant α9-EGFP, and the vertical axis shows reactivity with various antibodies. The reaction pattern of MA9-413 scFv-Fc differs only in hα9/mL1-EGFP, and the reactivity per expression amount is high as compared to other variants such as hα9-EGFP. hα9/mL1-EGFP is a variant wherein L1 region is substituted from a human sequence to a mouse sequence. Since MA9-413 reacts more strongly with mouse α9 than human α9, the results strongly suggest that the epitope of MA9-413 is L1 region.

Figure 10:
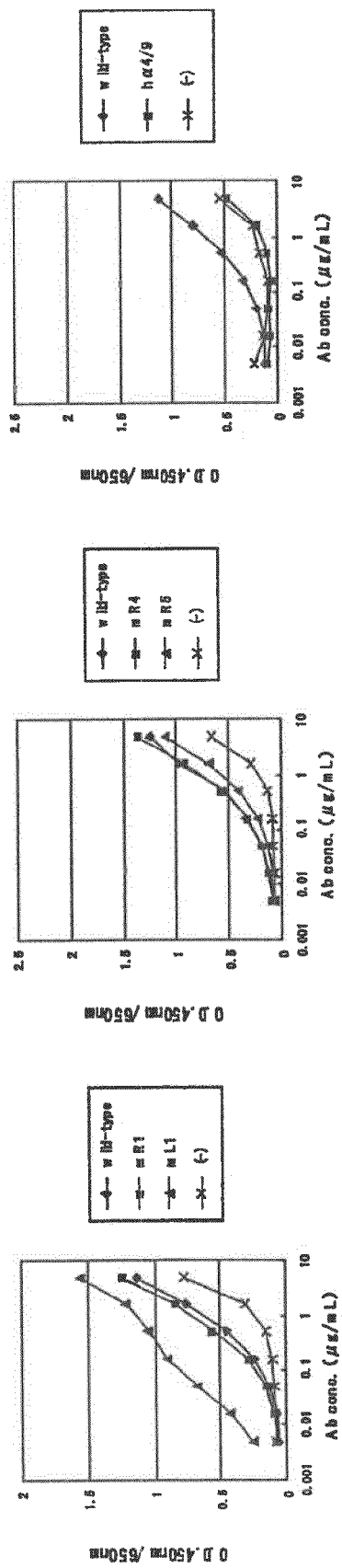
FIG. 10 is a graphic representation showing results of an analysis of the reactivity of MA9-413 scFv-Fc to altered α9 loop regions and altered α9 β propeller domains by ELISA.

Next, analysis by Cell ELISA was performed. Various cells after about 24 hr from gene transfection were collected, and seeded on a 96 well plate at $2\times10^4$ cells/100 μL/well. The rest was performed under the same conditions as in Example 11. As a result, as shown in FIG. 10, only hα9/mL1-EGFP tended to react higher with MA9-413 scFv-Fc than with wild-type hα9-EGFP. The results here also suggest that L1 region is an epitope of MA9-413.

As mentioned above, since structural information relating to α9 integrin is extremely poor, the significance of clarification for the first time of a neutralizing epitope is high. In addition, the impact of the results at this time indicating the possibility of the region named L1, which has not drawn attention in the α chain of other integrin families, playing an important function or capable of becoming a target for functional inhibition is considered to be huge.

Example 15

Efficacy Assessment of scFv-Fc For Mouse Arthritis Model-1 scFv-Fc of MA9-413, for which not only the reaction pattern but also epitope were found to be novel regions, was examined as to whether it can show efficacy for mouse arthritis model.

Figure 11:
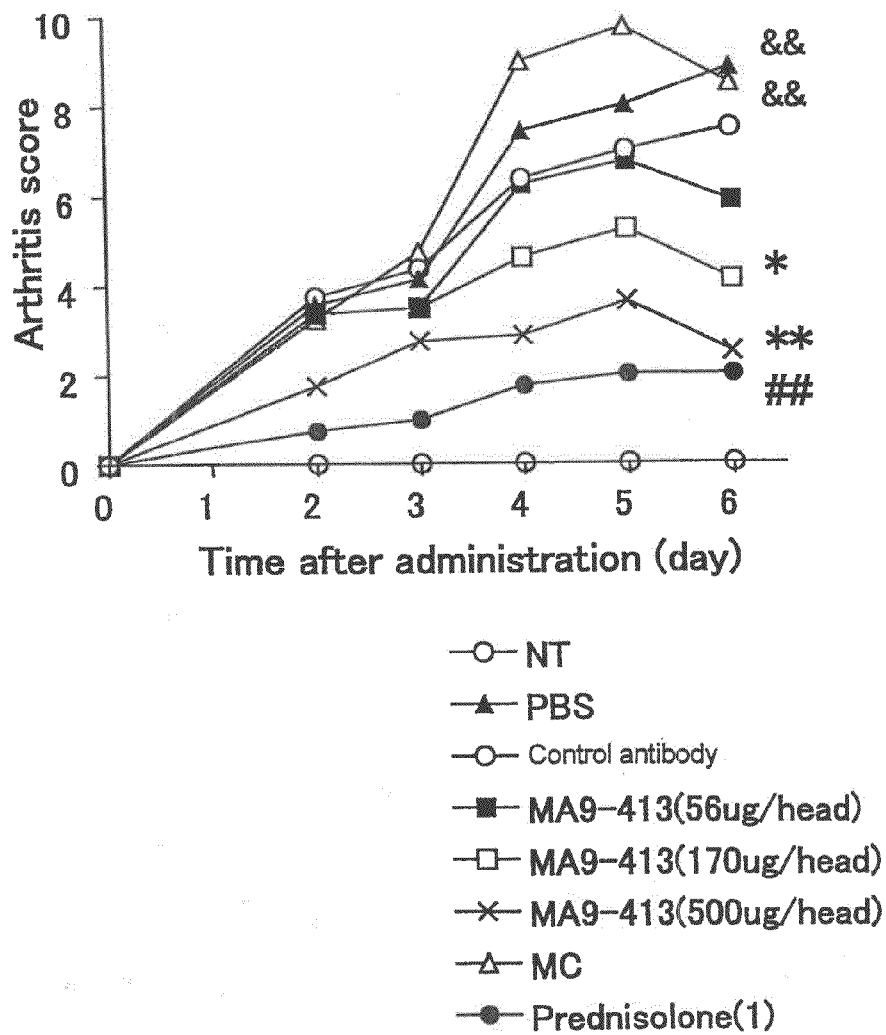
FIG. 11 is a graphic representation showing the suppressive effect of MA9-413 scFv-Fc on mouse collagen antibody-induced arthritis.

First, the effect on mouse collagen antibody-induced arthritis, which is one of the representative arthritis models, was examined. Anti-collagen antibody cocktail was administered to mouse, and LPS was administered 3 days later to induce the onset of arthritis. On the day of LPS administration and 3 days later, MA9-413 scFv-Fc was intraperitoneally administered at 500, 170 or 56 μg/head, and control mouse antibody was administered at 500 μg/head (4-8 mice per group). All the limbs of the mouse were observed with time and scored for swelling, and the mean value profile of each group is shown in the graph of FIG. 11. As a result, a concentration-dependent arthritis suppressive effect of MA9-413 scFv-Fc was recognized. In the score of the 500 μg/head administration group on Day 6, the suppression level was almost equivalent to that of the prednisolone administration group in the positive control groups, and sufficiently strong efficacy, namely, anti-inflammatory action, was confirmed.

Example 16

Efficacy Assessment of scFv-Fc for Mouse Arthritis Model-2

Next, whether MA9-413 scFv-Fc also shows efficacy for mouse collagen-induced arthritis, which is another representative arthritis model, was assessed. While inflammation reaction in the acute stage is induced in collagen antibody-induced arthritis in Example 15, it is known that chronic inflammatory response is induced in collagen-induced arthritis.

Figure 12:
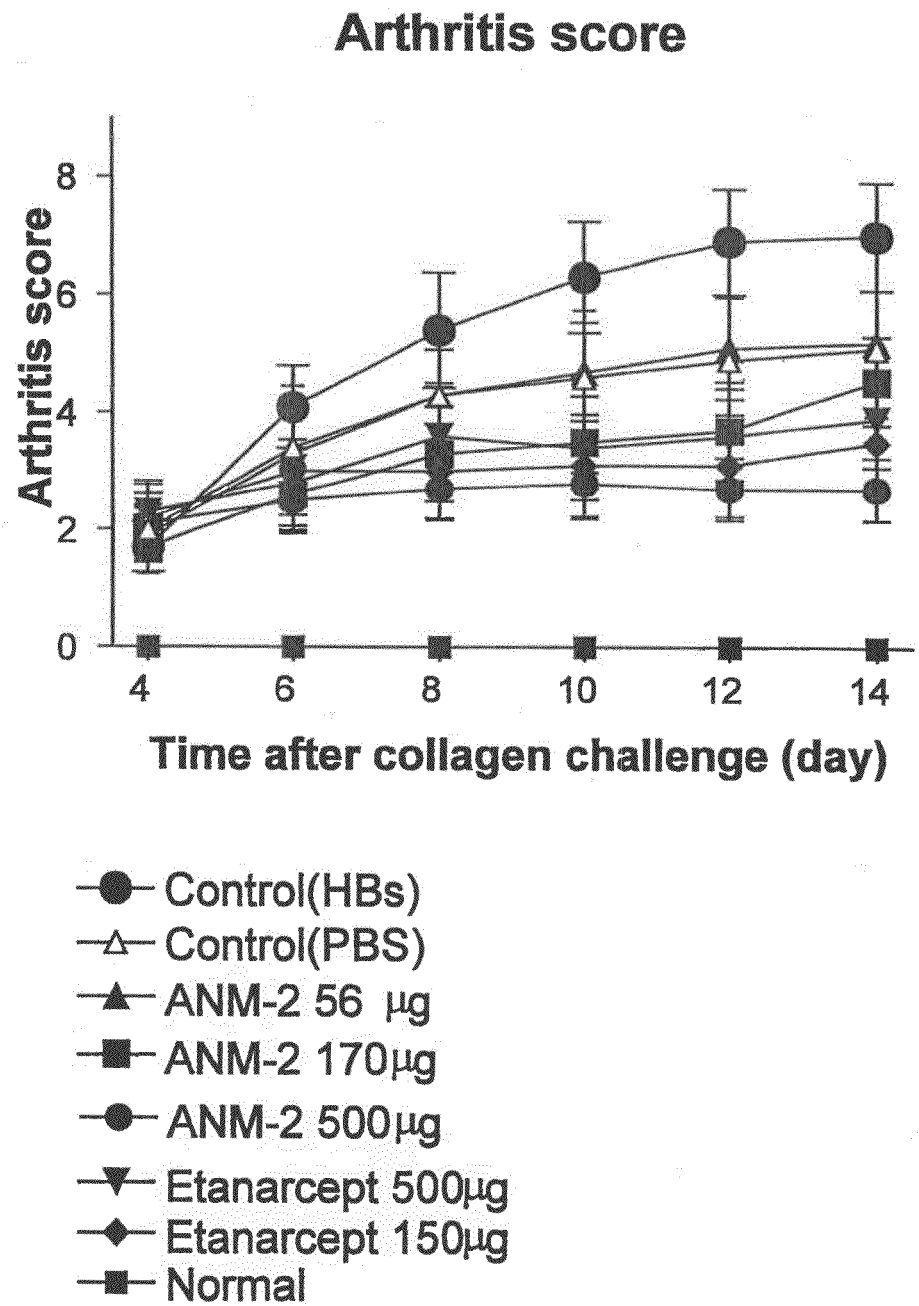
FIG. 12 is a graphic representation showing the suppressive effect of MA9-413 scFv-Fc on mouse collagen-induced arthritis. ANM-2 is an alternative name of MA9-413.

The onset of arthritis was induced by administering bovine type II collagen to mouse twice every 3 weeks. At 4 days, 6 days, 8 days, 10 days and 12 days from the second administration, MA9-413 scFv-Fc was intraperitoneally administered at 500, 170, 56 μg/head, a control mouse antibody was intraperitoneally administered at 500 μg/head, and etanercept was intraperitoneally administered at 500, 150 μg/head (10 mice per group) as a positive control. All the limbs of the mouse were observed with time and scored for tumentia, and the mean value profile of each group is shown in the graph of FIG. 12. ANM-2 is an alternative name of MA9-413. As a result, a concentration-dependent arthritis suppressive effect of MA9-413 scFv-Fc was recognized. In the 500 μg/head administration group, it was confirmed that the suppressive effect exceeded that in the etanercept 500 μg/head administration group in the positive control group and the efficacy was sufficiently strong.

Example 17

Efficacy Assessment of scFv-Fc for Osteoclast Differentiation

Furthermore, the effect for osteoclast differentiation in arthritis model was examined. In the mouse collagen antibody-induced arthritis used in the above-mentioned Example 15, bone marrow cells were collected from the femur of mouse the next day of administration of LPS which induces arthritis, and cultivated in an αMEM medium containing RANKL (final concentration 30 ng/mL) and M-CSF (final concentration 100 ng/mL) to induce differentiation of osteoclast. The culture medium was exchanged once 3 days from the start. On Day 7 from the start of the culture, TRAP (tartaric acid resistant acid phosphatase) staining was performed and the number of the stained cells was measured as osteoclast. As a negative control, an anti-HBs antibody was used. As a result, when MA9-413 (2 µg/mL) was added to the bone marrow cells of mouse having induced arthritis, differentiation to osteoclast was strongly suppressed (upper FIG. 13). In addition, when bone marrow cells, which were collected the next of intravenous administration of MA9-413 250 µg/head to the mouse simultaneously with LPS administration, were used, differentiation of osteoclast was suppressed (lower FIG. 13).

From the results of the above-mentioned Example 15 and Example 16, it was clarified that MA9-413 has an action to strongly suppress both acute stage and chronic stage inflammation reactions. From the results of the above-mentioned Example 17, moreover, it was strongly suggested that MA9-413 has, along with an anti-inflammatory effect, an articular destruction suppressive action during inflammation. Therefore, this clone is expected to be utilizable as a medicament more superior to conventional medicaments for the treatment or prophylaxis of human arthritis.

Example 18

Enhanced Affinity of MA9-413

Since MA9-413 is an antibody strongly reactive with mouse α9 rather than human α9, the affinity may not be sufficient for application to human arthritis. Therefore, enhancement of affinity was tried by molecular alteration of MA9-413. In most cases, in the antibody variable region, the region most strongly contributing to the antigen recognition is CDR3 region of VH. The sequence of CDR3 of VH of MA9-413 is as shown in SEQ ID NO: 4, wherein the cluster of Tyr is configured characteristically. A steric structural model of variable region of this clone was prepared and analyzed. As a result, it was found that the 108th Tyr and the 109th Tyr may be prominently configured particularly on the antigen binding surface. Therefore, to assess the role of the Tyr in the antigen recognition, expression vectors of variant scFv wherein the 108th Tyr was substituted by Ala (hereinafter to be referred to as MA9-418) and variant scFv wherein the 109th Tyr was substituted by Ala (hereinafter to be referred to as MA9-419) were constructed by a site-directed mutagenesis method.

scFv expressed by this vector was analyzed by Cell ELISA. As a result, MA9-418 showed improved reactivity with mouse α9 and human α9 as compared to MA9-413, and the reactivity of MA9-419 with mouse α9 and human α9 disappeared mostly. These results suggest that substitution of the 108th Tyr by an optimal amino acid improves reactivity with α9, and substitution of the 109th Tyr by other amino acid is not desirable since it is essential for antigen recognition.

Therefore, a specific clone was screened for with the reactivity with human α9 as an index, by an evolutionary engineering method (cycle of mutagenesis→culling-selection→amplification) such as site specific amino acid substitution of the 108th and error-prone PCR using Diversify PCR Random Mutagenesis Kit (Clontech). By performing plural selection steps, 3 clones of HA9-107, HA9-143 and HA9-212 with improved reactivity with human α9 were finally isolated.

The DNA base sequences of these clones were analyzed in the same manner as in Example 5 and amino acid sequences were deduced. The sequences of the clones are shown in FIG. 14.

Example 19

Expression and Purification of scFv

Using the above-mentioned clones MA9-418, HA9-107, HA9-143 and HA9-212 and *Escherichia coli* strain JM83 as a host of plasmid DNA, scFv was expressed and purified. The *Escherichia coli* transformant was cultured in 2×YT medium containing 2% glucose and 100 µg/mL ampicillin, IPTG was added in the logarithmic phase at a final concentration of 1 mM, and the cells were cultivated overnight to induce scFv expression. After completion of the culture, bacterial cells were recovered, suspended in 100 mM Tris-HCl solution (pH 7.4) containing 20% sucrose and 10 mM EDTA and the bacterial cells were stood still on ice for 30 min. Then, the cells were centrifuged at 8,900×g for 30 min, the supernatant was recovered, and the fraction obtained by filtration through 0.45 µm filter was taken as a periplasm fraction. Using the fraction as a starting material, scFv was purified according to a conventional method by RPAS Purification Module (Amersham), and the obtained elution fraction was dialyzed against PBS to give an scFv purification standard product.

Figure 15:
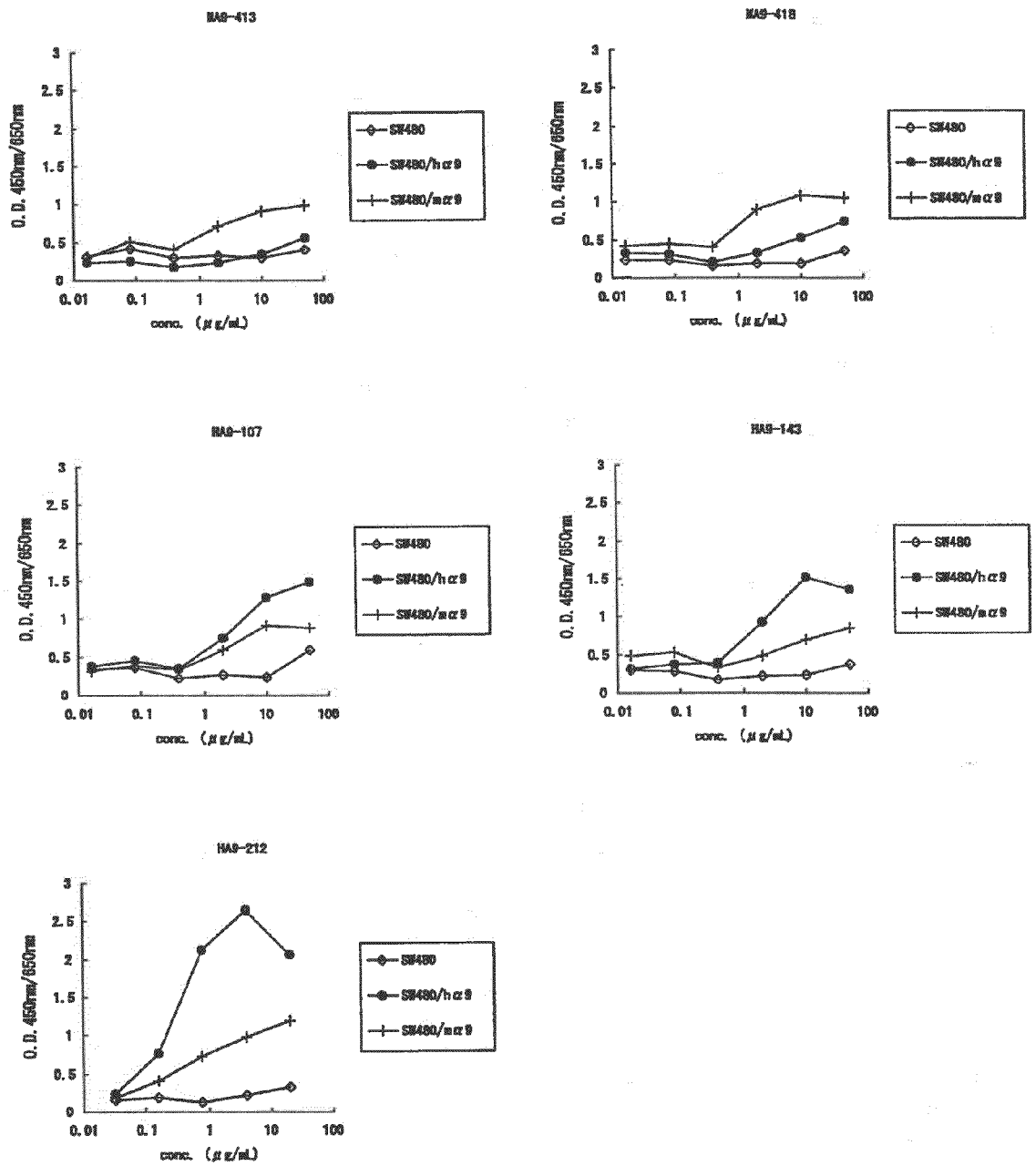
FIG. 15 is a graphic representation showing the reactivity of altered MA9-413 scFv to mouse α9 and human α9.

The reactivity of purified scFv was analyzed by Cell ELISA in the same manner as in Example 11 except that HRP-labeled anti-Etag antibody (Amersham) was used for the detection. As a result, as shown in FIG. 15, MA9-418, HA9-107, HA9-143 and HA9-212 showed improved reactivity with human α9 as compared to MA9-413, and particularly, HA9-212 showed a remarkable level of improvement.

Example 20

Construction, Expression and Purification of scFv-Fc

Using MA9-418, HA9-107, HA9-143 and HA9-212, scFv-Fc genes were constructed in the same manner as in Example 9.

scFv-Fc was expressed by transient expression using FreeStyle 293-F cell (Invitrogen) as a host. Transfection was performed using a 293 fectin reagent (Invitrogen), and the cell was cultured in a FreeStyle 293 expression medium (Invitrogen) for 2-3 days, and the culture supernatant was recovered by centrifugation and filtration with a 0.22 µm filter.

Purification was performed by Protein A column chromatography according to a conventional method. The scFv-Fc is solution obtained after PBS dialysis was taken as a purified product.

Figure 16:
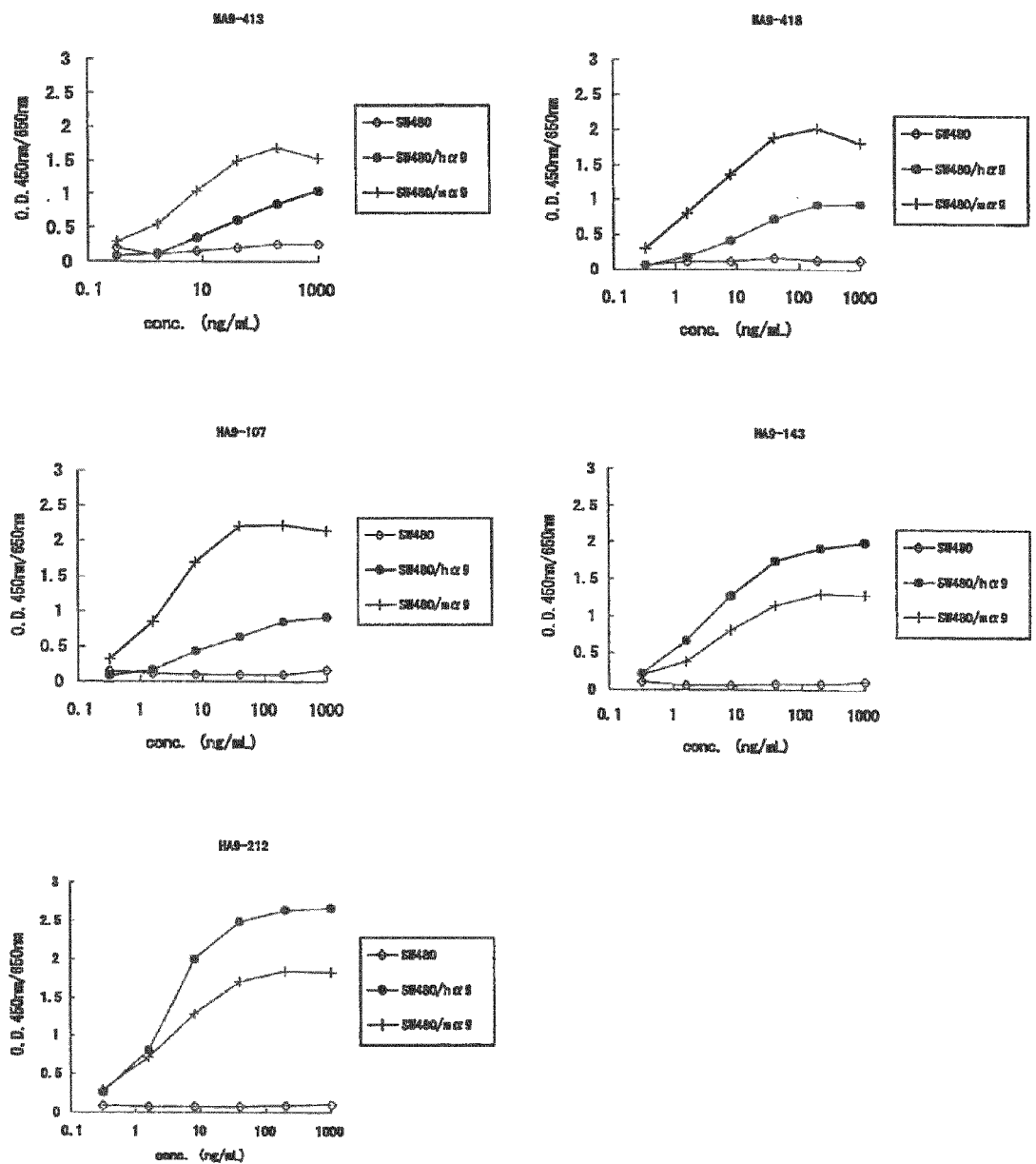
FIG. 16 is a graphic representation showing the reactivity of altered MA9-413 scFv-Fc to human α9 and mouse α9.

The reactivity of the prepared scFv-Fc purification product with mouse α9 and human α9 was analyzed by Cell ELISA in the same manner as in Example 11. As a result, MA9-418, HA9-107, HA9-143 and HA9-212 showed improved reactivity with human α9 as compared to MA9-413, as shown in FIG. 16.

Example 21

Analysis of Epitope Variant Clone

Figure 17:
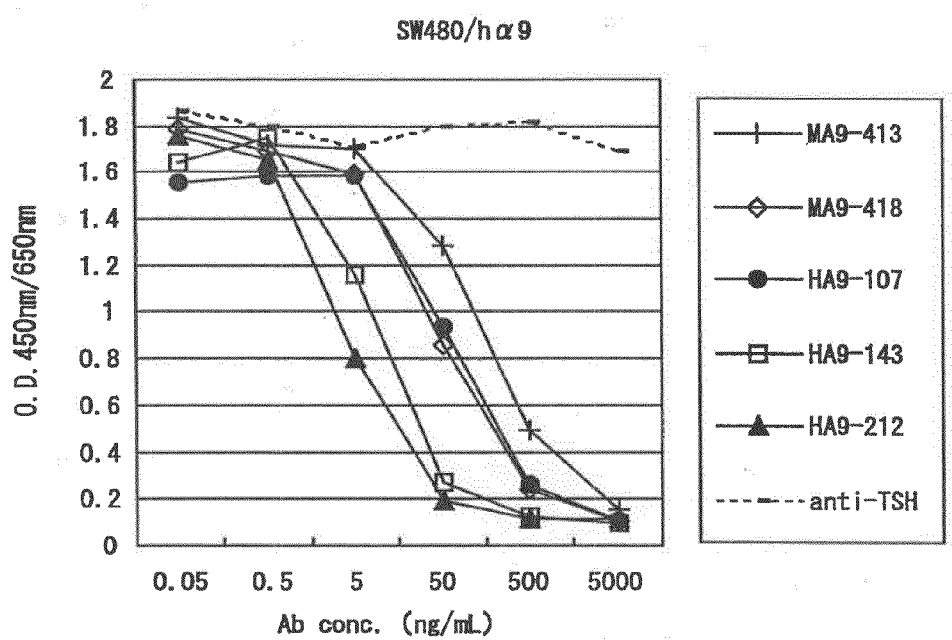
FIG. 17 is a graphic representation showing the competition inhibitory action of altered MA9-413 on the reactivity of MA9-413 to α9.

To examine whether MA9-418, HA9-107, HA9-143 and HA9-212 recognize L1 region of α9 in the same manner as in MA9-413, the following was examined. The concentration of MA9-413 phage antibody was set to a certain level, Cell ELISA was performed in the same manner as in Example 4, wherein scFv-Fc of each variant was serially diluted and added simultaneously with a sample, and the presence or absence of competitive inhibition of MA9-413 phage antibody was assessed. As a result, as shown in FIG. 17, concentration dependent-competitive inhibition was confirmed.

Hence, it has been strongly suggested that MA9-418, HA9-107, HA9-143 and HA9-212 recognize L1 region of α9, like MA9-413.

Example 22

Assessment of α9-Dependent Cell Adhesion Inhibitory Activity of Variant Clone scFv-Fc of each variant clone was assessed for inhibitory activity against human α9- and mouse α9-dependent cell adhesion in the same manner as in Example 13. Table 1 collectively shows IC50 values. It has been confirmed that all variant clones have a strong inhibitory activity against human α9 as compared to original MA9-413. Particularly, HA9-212 showed about 1000-fold higher inhibitory activity against human α9 as compared to MA9-413.

TABLE 1

|  | human α9 | mouse α9 |
|---|---|---|
| MA9-413 | 48.5 | 0.34 |
| HA9-418 | >10 | 0.96 |
| HA9-107 | >10 | 0.067 |
| HA9-143 | 0.42 | 2.32 |
| HA9-212 | 0.053 | 3.30 | unit: μg/mL

Example 23

Production and Preparation of IgG

Clone HA9-212 that showed the highest reactivity with human α9 was examined for the reactivity in the molecular form of IgG. Gene construction of IgG was performed according to the following procedures. First, the VH gene region of HA9-212 was amplified by PCR, and inserted into the cloning site of human H chain expression vector. In this vector, a leader sequence promoting extracellular secretory expression, VH gene, and a gene of human IgG1 constant region are connected, and the expression thereof is regulated by CAG promoter. In addition, this vector contains a neomycin resistance gene and an ampicillin resistance gene as drug resistance genes. Then, VL gene region of MA9-212 is amplified by PCR, and inserted into the cloning site of human L chain expression vector. In this vector, a leader sequence promoting extracellular secretory expression, VL gene, and a gene of human x chain constant region are connected, and the expression thereof is regulated by CAG promoter. The vector has dhfr gene and ampicillin resistance gene.

IgG was expressed by a transient expression using COS-7 cell and FreeStyle 293-F cell (Invitrogen) as hosts. Transfection into COS-7 cell was performed using Lipofectamine2000 (Invitrogen), and transfection into FreeStyle 293-F cell was performed using a 293 fectin reagent (Invitrogen) and, after culture for 2-3 days, the culture supernatant was recovered by centrifugation and filtration with a 0.22 μm filter.

Example 24

Analysis of Reactivity of IgG

Figure 18:
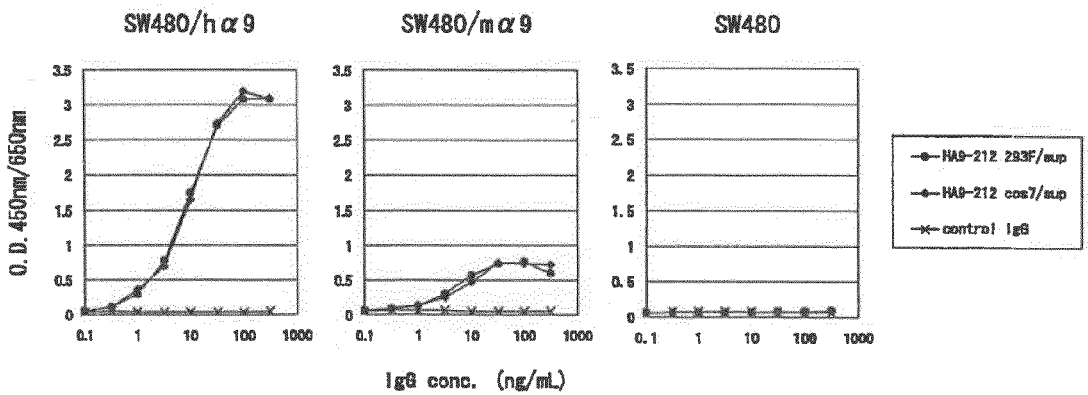
FIG. 18 is a graphic representation showing the reactivity of altered MA9-413 IgG to human α9 and mouse α9.

The IgG expression amount in the culture supernatant was quantified by human IgG quantification ELISA, and the reactivity with human α9 and mouse α9 at each IgG concentration was analyzed by Cell ELISA. HRP-labeled anti-human IgG (Fc) antibody (American Qualex) was used for detection, and the rest was performed under the same conditions as in Example 11. As a result, as shown in FIG. 18, concentration-dependent and specific reactivity with human α9 and mouse α9 was confirmed, and particularly, strong reactivity with human α9 was exhibited. From these results, it has been confirmed that HA9-212 shows reactivity with α9 even in the molecular form of IgG.

From the above results, it has been confirmed that MA9-418, HA9-107, HA9-143 and HA9-212, which were obtained by altering MA9-413, have reactivity with both mouse α9 and human α9, which MA9-413 has, and show greatly improved reactivity with human α9 and greatly improved inhibitory activity against human α9, while maintaining the L1 region recognition property. Furthermore, HA9-212 showed strong reactivity with human α9 even in the molecular form of IgG. From these, MA9-413 variant is expected to show great applicability as a medicament for the treatment or prophylaxis of human arthritis, which is superior to MA9-413.

INDUSTRIAL APPLICABILITY

Since the human monoclonal antibody and an antibody fragment thereof of the present invention have variable regions of human-derived anti-α9 integrin antibody, as well as specific reactivity with human and mouse α9 integrins, α9 integrin-dependent cell adhesion-inhibitory activity, and further, suppressive action against arthritis, they are expected to be utilizable as new drugs for the diagnosis, prophylaxis or treatment of various diseases involved by α9 integrins.

This application is based on patent application No. 2007-340203 filed in Japan (filing date: Dec. 28, 2007), the contents of which are incorporated in full herein.

The invention claimed is:

1. A human anti-α9 integrin antibody or antibody fragment that recognizes human α9 integrin and mouse α9 integrin and inhibits the interaction between the human and mouse α9 integrins and ligands, and that recognizes an epitope consisting of the region from the 104th Arg to the 122nd Asp of human α9 integrin of SEQ ID NO:36, and an epitope consisting of the region from the 105th Arg to the 123rd Asp of mouse α9 integrin of SEQ ID NO:37.

2. The antibody or antibody fragment according to claim 1, comprising (a) heavy-chain complementarity determining regions and (b) light-chain complementarity determining regions, CDR1, CDR2, and CDR3, wherein the regions consist of the amino acid sequences, respectively, as follows:
   (a) Heavy-chain complementarity determining regions, CDR1, CDR2, and CDR3
      SEQ ID NO:2, SEQ ID NO:3, and SEQ ID NO:4;
      SEQ ID NO:13, SEQ ID NO:14, and SEQ ID NO:15;
      SEQ ID NO:19, SEQ ID NO:20, and SEQ ID NO:21;
      SEQ ID NO:25, SEQ ID NO:26, and SEQ ID NO:27; or
      SEQ ID NO:31, SEQ ID NO:32, and SEQ ID NO:33; and
   (b) light-chain complementarity determining regions, CDR1, CDR2, and CDR3
      SEQ ID NO:7, SEQ ID NO:8, and SEQ ID NO:9.

3. The antibody or antibody fragment according to claim 2, comprising heavy-chain complementarity determining regions, CDR1, CDR2, and CDR3, wherein the regions consist of the amino acid sequences of SEQ ID NO:31, SEQ ID NO:32, and SEQ ID NO:33, respectively.

4. The antibody or antibody fragment according to claim 1, comprising a heavy-chain variable region consisting of the amino acid sequence of any one of SEQ ID NO:1, SEQ ID NO:12, SEQ ID NO:18, SEQ ID NO:24, and SEQ ID NO:30, and a light-chain variable region consisting of the amino acid sequence of SEQ ID NO:6.

5. The antibody or antibody fragment according to claim 4, comprising a heavy-chain variable region consisting of the amino acid sequence of SEQ ID NO:30.

6. The human anti-α9 integrin antibody according to claim 1, wherein the antibody is a complete antibody.

7. The human anti-α9 integrin antibody fragment according to claim 1, wherein the antibody fragment is scFv or scFv-Fc.

8. A composition comprising the antibody or antibody fragment according to claim 1 and a carrier or additive.

9. A method of treating rheumatoid arthritis in a subject, comprising administering a therapeutically effective amount of the antibody or antibody fragment according to claim 1 to the subject.

10. A method of producing a composition, comprising mixing the antibody or antibody fragment according to claim 1 with a carrier or additive.

* * * * *

SEQUENCE LISTING

<160> NUMBER OF SEQ ID NOS: 40

<210> SEQ ID NO 1
<211> LENGTH: 126
<212> TYPE: PRT
<213> ORGANISM: Homo sapiens

<400> SEQUENCE: 1

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Ala Phe Gly Asp Tyr
            20                  25                  30

```
Gly Met Ser Trp Val Arg Gln Ala Pro Gly Lys Gly Leu Glu Trp Val
            35                  40                  45

Ser Gly Ile Asn Trp Asn Gly Gly Ser Thr Gly Tyr Ala Asp Ser Val
 50                  55                  60

Lys Gly Arg Phe Thr Thr Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Asp Glu Asn Tyr Asp Ile Leu Thr Gly Tyr Tyr Tyr Tyr Gly
                100                 105                 110

Met Asp Val Trp Gly Gln Gly Thr Thr Val Thr Val Ser Ser
        115                 120                 125

<210> SEQ ID NO 2
<211> LENGTH: 5
<212> TYPE: PRT
<213> ORGANISM: Homo sapiens

<400> SEQUENCE: 2

Asp Tyr Gly Met Ser
 1               5

<210> SEQ ID NO 3
<211> LENGTH: 17
<212> TYPE: PRT
<213> ORGANISM: Homo sapiens

<400> SEQUENCE: 3

Gly Ile Asn Trp Asn Gly Gly Ser Thr Gly Tyr Ala Asp Ser Val Lys
 1               5                  10                  15

Gly

<210> SEQ ID NO 4
<211> LENGTH: 17
<212> TYPE: PRT
<213> ORGANISM: Homo sapiens

<400> SEQUENCE: 4

Asp Glu Asn Tyr Asp Ile Leu Thr Gly Tyr Tyr Tyr Tyr Gly Met Asp
 1               5                  10                  15

Val

<210> SEQ ID NO 5
<211> LENGTH: 378
<212> TYPE: DNA
<213> ORGANISM: Homo sapiens

<400> SEQUENCE: 5
gaggtgcagc tggtggagtc tgggggaggt gtggtacggc ctgggggtc cctgagactc      60 tcctgtgcag cctctggatt cgcctttggt gattatggca tgagctgggt ccgccaagct    120
ccagggaagg gctggagtg gtctctggt attaattgga atggtggtag cacaggttat     180
gcagactctg tgaagggccg attcaccacc tccagagaca cgccaagaa ctccctgtat    240 ctgcaaatga acagtctgag agccgaggac acggccttgt attactgtgc gagagatgag    300
aattacgata ttttgactgg ttactactac tacggtatgg acgtctgggg ccaagggacc    360
acggtcaccg tctcctca                                                  378
```

```
<210> SEQ ID NO 6
<211> LENGTH: 111
<212> TYPE: PRT
<213> ORGANISM: Homo sapiens

<400> SEQUENCE: 6

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Thr Val Trp Ala Phe Gly Gly Gly Thr Lys Leu Thr Val Leu Gly
            100                 105                 110

<210> SEQ ID NO 7
<211> LENGTH: 13
<212> TYPE: PRT
<213> ORGANISM: Homo sapiens

<400> SEQUENCE: 7

Ser Gly Ser Ser Ser Asn Ile Gly Asn Asn Tyr Val Ser
1               5                   10

<210> SEQ ID NO 8
<211> LENGTH: 7
<212> TYPE: PRT
<213> ORGANISM: Homo sapiens

<400> SEQUENCE: 8

Asp Asn Asn Lys Arg Pro Ser
1               5

<210> SEQ ID NO 9
<211> LENGTH: 7
<212> TYPE: PRT
<213> ORGANISM: Homo sapiens

<400> SEQUENCE: 9

Gly Thr Trp Asp Ser Ser Leu
1               5

<210> SEQ ID NO 10
<211> LENGTH: 333
<212> TYPE: DNA
<213> ORGANISM: Homo sapiens

<400> SEQUENCE: 10
cagtctgtcg tgacgcagcc gccctcagtg tctgcggccc caggacagaa ggtcaccatc     60
tcctgctctg gaagcagctc caacattggc aataattatg tatcctggta ccaacaactc    120
ccaggaacag ccccaaaact cctcatttat gacaataata gagagaccgtc agggattcct   180 gaccgattct ctgcctccaa gtctggcacg tcagccaccc tgggcatcac cggactccag    240
actggggacg aggccgatta ttactgcgga acatgggata gcagcctgac tgtctgggcc    300
ttcggcggtg ggaccaagct gaccgtccta ggt                                 333
```

<210> SEQ ID NO 11
<211> LENGTH: 756
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

| | | |
|---|---|---|
| gaggtgcagc tggtggagtc tgggggaggt gtggtacggc ctgggggggtc cctgagactc | 60 |
| tcctgtgcag cctctggatt cgcctttggt gattatggca tgagctgggt ccgccaagct | 120 |
| ccagggaagg gctggagtg gtctctggt attaattgga atggtggtag cacaggttat | 180 |
| gcagactctg tgaagggccg attcaccacc tccagagaca cgccaagaa ctccctgtat | 240 |
| ctgcaaatga acagtctgag agccgaggac acggccttgt attactgtgc gagagatgag | 300 |
| aattacgata ttttgactgg ttactactac tacggtatgg acgtctgggg ccaagggacc | 360 |
| acggtcaccg tctcctcagg tgaggcggt tcaggcggag gtggctctgg cggtggcgga | 420 |
| tcgcagtctg tcgtgacgca gccgccctca gtgtctgcgg ccccaggaca aaggtcacc | 480 |
| atctcctgct ctggaagcag ctccaacatt ggcaataatt atgtatcctg gtaccaacaa | 540 |
| ctcccaggaa cagcccccaa actcctcatt tatgacaata taagagacc gtcagggatt | 600 |
| cctgaccgat tctctgcctc caagtctggc acgtcagcca ccctgggcat caccggactc | 660 |
| cagactgggg acgaggccga ttattactgc ggaacatggg atagcagcct gactgtctgg | 720 |
| gccttcggcg gtgggaccaa gctgaccgtc ctaggt | 756 |

<210> SEQ ID NO 12
<211> LENGTH: 126
<212> TYPE: PRT
<213> ORGANISM: Homo sapiens

<400> SEQUENCE: 12

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Ala Phe Gly Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Thr Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Glu Asn Tyr Asp Ile Leu Thr Gly Tyr Tyr Tyr Gly
            100                 105                 110

Met Asp Val Trp Gly Gln Gly Thr Thr Val Thr Val Ser Ser
        115                 120                 125

<210> SEQ ID NO 13
<211> LENGTH: 5
<212> TYPE: PRT
<213> ORGANISM: Homo sapiens

<400> SEQUENCE: 13

Asp Tyr Gly Met Ser
1               5

```
<210> SEQ ID NO 14
<211> LENGTH: 17
<212> TYPE: PRT
<213> ORGANISM: Homo sapiens

<400> SEQUENCE: 14

Gly Ile Asn Trp Asn Gly Gly Ser Thr Gly Tyr Ala Asp Ser Val Lys
1               5                   10                  15

Gly

<210> SEQ ID NO 15
<211> LENGTH: 17
<212> TYPE: PRT
<213> ORGANISM: Homo sapiens

<400> SEQUENCE: 15

Asp Glu Asn Tyr Asp Ile Leu Thr Gly Ala Tyr Tyr Tyr Gly Met Asp
1               5                   10                  15

Val

<210> SEQ ID NO 16
<211> LENGTH: 378
<212> TYPE: DNA
<213> ORGANISM: Homo sapiens

<400> SEQUENCE: 16
gaggtgcagc tggtggagtc tgggggaggt gtggtacggc ctgggggtc cctgagactc      60 tcctgtgcag cctctggatt cgcctttggt gattatggca tgagctgggt ccgccaagct    120
ccagggaagg ggctggagtg ggtctctggt attaattgga atggtggtag cacaggttat    180
gcagactctg tgaagggccg attcaccacc tccagagaca cgccaagaa ctccctgtat     240 ctgcaaatga acagtctgag agccgaggac acggccttgt attactgtgc gagagatgag    300
aattacgata ttttgactgg tgcctactac tacggtatgg acgtctgggg ccaagggacc    360
acggtcaccg tctcctca                                                   378

<210> SEQ ID NO 17
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gaggtgcagc tggtggagtc tgggggaggt gtggtacggc ctgggggtc cctgagactc      60 tcctgtgcag cctctggatt cgcctttggt gattatggca tgagctgggt ccgccaagct    120
ccagggaagg ggctggagtg ggtctctggt attaattgga atggtggtag cacaggttat    180
gcagactctg tgaagggccg attcaccacc tccagagaca cgccaagaa ctccctgtat     240 ctgcaaatga acagtctgag agccgaggac acggccttgt attactgtgc gagagatgag    300
aattacgata ttttgactgg tgcctactac tacggtatgg acgtctgggg ccaagggacc    360
acggtcaccg tctcctcagg tggaggcggt tcaggcggag gtggctctgg cggtggcgga    420
tcgcagtctg tcgtgacgca gccgcccctca gtgtctgcgg ccccaggaca gaaggtcacc   480
atctcctgct ctggaagcag ctccaacatt ggcaataatt atgtatcctg gtaccaacaa    540
ctcccaggaa cagcccccaa actcctcatt tatgacaata taagagacc gtcagggatt     600 cctgaccgat tctctgcctc caagtctggc acgtcagcca cctgggcat caccggactc     660
```

```
cagactgggg acgaggccga ttattactgc ggaacatggg atagcagcct gactgtctgg    720
gccttcggcg gtgggaccaa gctgaccgtc ctaggt                              756
```

<210> SEQ ID NO 18
<211> LENGTH: 126
<212> TYPE: PRT
<213> ORGANISM: Homo sapiens

<400> SEQUENCE: 18

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Ala Phe Gly Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Thr Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Glu Asn Tyr Asp Ile Leu Thr Asn Glu Tyr Tyr Tyr Gly
            100                 105                 110

Met Asp Val Trp Gly Gln Gly Thr Thr Val Thr Val Ser Ser
        115                 120                 125
```

<210> SEQ ID NO 19
<211> LENGTH: 5
<212> TYPE: PRT
<213> ORGANISM: Homo sapiens

<400> SEQUENCE: 19

```
Asp Tyr Gly Met Ser
1               5
```

<210> SEQ ID NO 20
<211> LENGTH: 17
<212> TYPE: PRT
<213> ORGANISM: Homo sapiens

<400> SEQUENCE: 20

```
Gly Ile Asn Trp Asn Gly Gly Ser Thr Gly Tyr Ala Asp Ser Val Lys
1               5                   10                  15

Gly
```

<210> SEQ ID NO 21
<211> LENGTH: 17
<212> TYPE: PRT
<213> ORGANISM: Homo sapiens

<400> SEQUENCE: 21

```
Asp Glu Asn Tyr Asp Ile Leu Thr Asn Glu Tyr Tyr Tyr Gly Met Asp
1               5                   10                  15

Val
```

<210> SEQ ID NO 22
<211> LENGTH: 378
<212> TYPE: DNA
<213> ORGANISM: Homo sapiens

<400> SEQUENCE: 22

```
gaggtgcagc tggtggagtc tgggggaggt gtggtacggc ctggggggtc cctgagactc    60
tcctgtgcag cctctggatt cgcctttggt gattatggca tgagctgggt ccgccaagct   120
ccagggaagg ggctggagtg ggtctctggt attaattgga atggtggtag cacaggttat   180
gcagactctg tgaagggccg attcaccacc tccagagaca cgccaagaa ctccctgtat    240 ctgcaaatga acagtctgag agccgaggac acggccttgt attactgtgc gagagatgag   300
aattacgata ttttgactaa tgagtactac tatggtatgg atgtctgggg tcaagggacc   360
acggtcaccg tctcctca                                                 378
```

<210> SEQ ID NO 23
<211> LENGTH: 756
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
gaggtgcagc tggtggagtc tgggggaggt gtggtacggc ctggggggtc cctgagactc    60
tcctgtgcag cctctggatt cgcctttggt gattatggca tgagctgggt ccgccaagct   120
ccagggaagg ggctggagtg ggtctctggt attaattgga atggtggtag cacaggttat   180
gcagactctg tgaagggccg attcaccacc tccagagaca cgccaagaa ctccctgtat    240 ctgcaaatga acagtctgag agccgaggac acggccttgt attactgtgc gagagatgag   300
aattacgata ttttgactaa tgagtactac tatggtatgg atgtctgggg tcaagggacc   360
acggtcaccg tctcctcagg tggaggcggt tcaggcggag gtggctctgg cggtggcgga   420
tcgcagtctg tcgtgacgca gccgccctca gtgtctgcgg ccccaggaca gaaggtcacc   480
atctcctgct ctggaagcag ctccaacatt ggcaataatt atgtatcctg gtaccaacaa   540
ctcccaggaa cagcccccaa actcctcatt tatgacaata taagagacc gtcagggatt    600 cctgaccgat tctctgcctc caagtctggc acgtcagcca ccctgggcat caccggactc   660
cagactgggg acgaggccga ttattactgc ggaacatggg atagcagcct gactgtctgg   720
gccttcggcg gtgggaccaa gctgaccgtc ctaggt                             756
```

<210> SEQ ID NO 24
<211> LENGTH: 126
<212> TYPE: PRT
<213> ORGANISM: Homo sapiens

<400> SEQUENCE: 24

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Ala Phe Gly Glu Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Thr Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Glu Asn Tyr Asp Ile Leu Thr Gly His Tyr Tyr Tyr Gly
            100                 105                 110

Met Asp Val Trp Gly Gln Gly Thr Thr Val Thr Val Ser Ser
        115                 120                 125

<210> SEQ ID NO 25
<211> LENGTH: 5
<212> TYPE: PRT
<213> ORGANISM: Homo sapiens

<400> SEQUENCE: 25

Glu Tyr Gly Met Ser
1               5

<210> SEQ ID NO 26
<211> LENGTH: 17
<212> TYPE: PRT
<213> ORGANISM: Homo sapiens

<400> SEQUENCE: 26

Gly Ile Asn Trp Asn Gly Gly Ser Thr Gly Tyr Ala Asp Ser Val Lys
1               5                   10                  15

Gly

<210> SEQ ID NO 27
<211> LENGTH: 17
<212> TYPE: PRT
<213> ORGANISM: Homo sapiens

<400> SEQUENCE: 27

Asp Glu Asn Tyr Asp Ile Leu Thr Gly His Tyr Tyr Tyr Gly Met Asp
1               5                   10                  15

Val

<210> SEQ ID NO 28
<211> LENGTH: 378
<212> TYPE: DNA
<213> ORGANISM: Homo sapiens

<400> SEQUENCE: 28
gaggtgcagc tggtggagtc tgggggaggt gtggtacggc ctgggggtc cctgagactc      60 tcctgtgcag cctctggatt cgcctttggt gaatatggca tgagctgggt ccgccaagct    120
ccagggaagg ggctggagtg ggtctctggt attaattgga atggtggtag cacaggttat    180
gcagactctg tgaagggccg attcaccacc tccagagaca acgccaagaa ctccctgtat    240
ctgcaaatga acagtctgag agccgaggac acggccttgt attactgtgc gagagatgag    300
aattacgata ttttgactgg gcattactac tatggtatgg atgtctgggg tcaagggacc    360
acggtcaccg tctcctca                                                  378

<210> SEQ ID NO 29
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gaggtgcagc tggtggagtc tgggggaggt gtggtacggc ctgggggtc cctgagactc      60 tcctgtgcag cctctggatt cgcctttggt gaatatggca tgagctgggt ccgccaagct    120
ccagggaagg ggctggagtg ggtctctggt attaattgga atggtggtag cacaggttat    180

```
gcagactctg tgaagggccg attcaccacc tccagagaca acgccaagaa ctccctgtat    240
ctgcaaatga acagtctgag agccgaggac acggccttgt attactgtgc gagagatgag    300
aattacgata ttttgactgg gcattactac tatggtatgg atgtctgggg tcaagggacc    360
acggtcaccg tctcctcagg tggaggcggt tcaggcggag gtggctctgg cggtggcgga    420
tcgcagtctg tcgtgacgca gccgccctca gtgtctgcgg ccccaggaca gaaggtcacc    480
atctcctgct ctggaagcag ctccaacatt ggcaataatt atgtatcctg gtaccaacaa    540
ctcccaggaa cagcccccaa actcctcatt tatgacaata taagagaccg tcagggatt     600 cctgaccgat tctctgcctc caagtctggc acgtcagcca ccctgggcat caccggactc    660
cagactgggg acgaggccga ttattactgc ggaacatggg atagcagcct gactgtctgg    720
gccttcggcg gtgggaccaa gctgaccgtc ctaggt                              756
```

<210> SEQ ID NO 30
<211> LENGTH: 126
<212> TYPE: PRT
<213> ORGANISM: Homo sapiens

<400> SEQUENCE: 30

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Ala Phe Gly Glu Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Gln Gly Arg Phe Thr Thr Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Glu Asn Tyr Asp Ile Leu Thr Gly Asn Tyr Tyr Tyr Gly
            100                 105                 110

Met Asp Val Trp Gly Gln Gly Thr Thr Val Thr Val Ser Ser
        115                 120                 125
```

<210> SEQ ID NO 31
<211> LENGTH: 5
<212> TYPE: PRT
<213> ORGANISM: Homo sapiens

<400> SEQUENCE: 31

```
Glu Tyr Gly Met Ser
1               5
```

<210> SEQ ID NO 32
<211> LENGTH: 17
<212> TYPE: PRT
<213> ORGANISM: Homo sapiens

<400> SEQUENCE: 32

```
Gly Ile Asn Trp Asn Gly Gly Ser Thr Gly Tyr Ala Asp Ser Val Gln
1               5                   10                  15

Gly
```

<210> SEQ ID NO 33
<211> LENGTH: 17
<212> TYPE: PRT

-continued

<213> ORGANISM: Homo sapiens

<400> SEQUENCE: 33

Asp Glu Asn Tyr Asp Ile Leu Thr Gly Asn Tyr Tyr Tyr Gly Met Asp
1               5                   10                  15
Val

<210> SEQ ID NO 34
<211> LENGTH: 378
<212> TYPE: DNA
<213> ORGANISM: Homo sapiens

<400> SEQUENCE: 34

```
gaggtgcagc tggtggagtc tgggggaggt gtggtacggc ctggggggtc cctgagactc    60
tcctgtgcag cctctggatt cgcctttggt gagtatggca tgagctgggt ccgccaagct   120
ccagggaagg ggctggagtg ggtctctggt attaattgga atggtggtag cacaggttat   180
gcagactctg tgcagggccg attcaccacc tccagagaca cgccaagaa ctccctgtat    240
ctgcaaatga acagtctgag agccgaggac acggccttgt attactgtgc gagagatgag   300
aattacgata ttttgactgg taactactac tacggtatgg acgtctgggg ccaagggacc   360
acggtcaccg tctcctca                                                 378
```

<210> SEQ ID NO 35
<211> LENGTH: 756
<212> TYPE: DNA
<213> ORGANISM: Homo sapiens

<400> SEQUENCE: 35

```
gaggtgcagc tggtggagtc tgggggaggt gtggtacggc ctggggggtc cctgagactc    60
tcctgtgcag cctctggatt cgcctttggt gagtatggca tgagctgggt ccgccaagct   120
ccagggaagg ggctggagtg ggtctctggt attaattgga atggtggtag cacaggttat   180
gcagactctg tgcagggccg attcaccacc tccagagaca cgccaagaa ctccctgtat    240
ctgcaaatga acagtctgag agccgaggac acggccttgt attactgtgc gagagatgag   300
aattacgata ttttgactgg taactactac tacggtatgg acgtctgggg ccaagggacc   360
acggtcaccg tctcctcagg tggaggcggt tcaggcggag gtggctctgg cggtggcgga   420
tcgcagtctg tcgtgacgca gccgccctca gtgtctgcgg ccccaggaca aaggtcacc    480
atctcctgct ctggaagcag ctccaacatt ggcaataatt atgtatcctg gtaccaacaa   540
ctcccaggaa cagcccccaa actcctcatt tatgacaata taagagacc gtcagggatt    600
cctgaccgat tctctgcctc caagtctggc acgtcagcca ccctgggcat caccggactc   660
cagactgggg acgaggccga ttattactgc ggaacatggg atagcagcct gactgtctgg   720
gccttcggcg gtgggaccaa gctgaccgtc ctaggt                             756
```

<210> SEQ ID NO 36
<211> LENGTH: 1035
<212> TYPE: PRT
<213> ORGANISM: Homo sapiens

<400> SEQUENCE: 36

Met Gly Gly Pro Ala Ala Pro Arg Gly Ala Gly Arg Leu Arg Ala Leu
1               5                   10                  15
Leu Leu Ala Leu Val Val Ala Gly Ile Pro Ala Gly Ala Tyr Asn Leu
            20                  25                  30
Asp Pro Gln Arg Pro Val His Phe Gln Gly Pro Ala Asp Ser Phe Phe

```
                35                  40                  45
Gly Tyr Ala Val Leu Glu His Phe His Asp Asn Thr Arg Trp Val Leu
 50                  55                  60

Val Gly Ala Pro Lys Ala Asp Ser Lys Tyr Ser Pro Ser Val Lys Ser
 65                  70                  75                  80

Pro Gly Ala Val Phe Lys Cys Arg Val His Thr Asn Pro Asp Arg Arg
                 85                  90                  95

Cys Thr Glu Leu Asp Met Ala Arg Gly Lys Asn Arg Gly Thr Ser Cys
                100                 105                 110

Gly Lys Thr Cys Arg Glu Asp Arg Asp Asp Glu Trp Met Gly Val Ser
                115                 120                 125

Leu Ala Arg Gln Pro Lys Ala Asp Gly Arg Val Leu Ala Cys Ala His
                130                 135                 140

Arg Trp Lys Asn Ile Tyr Tyr Glu Ala Asp His Ile Leu Pro His Gly
145                 150                 155                 160

Phe Cys Tyr Ile Ile Pro Ser Asn Leu Gln Ala Lys Gly Arg Thr Leu
                165                 170                 175

Ile Pro Cys Tyr Glu Glu Tyr Lys Lys Lys Tyr Gly Glu Glu His Gly
                180                 185                 190

Ser Cys Gln Ala Gly Ile Ala Gly Phe Phe Thr Glu Glu Leu Val Val
                195                 200                 205

Met Gly Ala Pro Gly Ser Phe Tyr Trp Ala Gly Thr Ile Lys Val Leu
210                 215                 220

Asn Leu Thr Asp Asn Thr Tyr Leu Lys Leu Asn Asp Glu Val Ile Met
225                 230                 235                 240

Asn Arg Arg Tyr Thr Tyr Leu Gly Tyr Ala Val Thr Ala Gly His Phe
                245                 250                 255

Ser His Pro Ser Thr Ile Asp Val Val Gly Gly Ala Pro Gln Asp Lys
                260                 265                 270

Gly Ile Gly Lys Val Tyr Ile Phe Arg Ala Asp Arg Arg Ser Gly Thr
                275                 280                 285

Leu Ile Lys Ile Phe Gln Ala Ser Gly Lys Lys Met Gly Ser Tyr Phe
290                 295                 300

Gly Ser Ser Leu Cys Ala Val Asp Leu Asn Gly Asp Gly Leu Ser Asp
305                 310                 315                 320

Leu Leu Val Gly Ala Pro Met Phe Ser Glu Ile Arg Asp Glu Gly Gln
                325                 330                 335

Val Thr Val Tyr Ile Asn Arg Gly Asn Gly Ala Leu Glu Glu Gln Leu
                340                 345                 350

Ala Leu Thr Gly Asp Gly Ala Tyr Asn Ala His Phe Gly Glu Ser Ile
                355                 360                 365

Ala Ser Leu Asp Asp Leu Asp Asn Asp Gly Phe Pro Asp Val Ala Ile
                370                 375                 380

Gly Ala Pro Lys Glu Asp Asp Phe Ala Gly Ala Val Tyr Ile Tyr His
385                 390                 395                 400

Gly Asp Ala Gly Gly Ile Val Pro Gln Tyr Ser Met Lys Leu Ser Gly
                405                 410                 415

Gln Lys Ile Asn Pro Val Leu Arg Met Phe Gly Gln Ser Ile Ser Gly
                420                 425                 430

Gly Ile Asp Met Asp Gly Asn Gly Tyr Pro Asp Val Thr Val Gly Ala
                435                 440                 445

Phe Met Ser Asp Ser Val Val Leu Leu Arg Ala Arg Pro Val Ile Thr
450                 455                 460
```

```
Val Asp Val Ser Ile Phe Leu Pro Gly Ser Ile Asn Ile Thr Ala Pro
465                 470                 475                 480

Gln Cys His Asp Gly Gln Gln Pro Val Asn Cys Leu Asn Val Thr Thr
            485                 490                 495

Cys Phe Ser Phe His Gly Lys His Val Pro Glu Glu Ile Gly Leu Asn
        500                 505                 510

Tyr Val Leu Met Ala Asp Val Ala Lys Lys Glu Lys Gly Gln Met Pro
        515                 520                 525

Arg Val Tyr Phe Val Leu Leu Gly Glu Thr Met Gly Gln Val Thr Glu
        530                 535                 540

Lys Leu Gln Leu Thr Tyr Met Glu Glu Thr Cys Arg His Tyr Val Ala
545                 550                 555                 560

His Val Lys Arg Arg Val Gln Asp Val Ile Ser Pro Ile Val Phe Glu
            565                 570                 575

Ala Ala Tyr Ser Leu Ser Glu His Val Thr Gly Glu Glu Arg Glu
        580                 585                 590

Leu Pro Pro Leu Thr Pro Val Leu Arg Trp Lys Lys Gly Gln Lys Ile
        595                 600                 605

Ala Gln Lys Asn Gln Thr Val Phe Glu Arg Asn Cys Arg Ser Glu Asp
610                 615                 620

Cys Ala Ala Asp Leu Gln Leu Gln Gly Lys Leu Leu Leu Ser Ser Met
625                 630                 635                 640

Asp Glu Lys Thr Leu Tyr Leu Ala Leu Gly Ala Val Lys Asn Ile Ser
            645                 650                 655

Leu Asn Ile Ser Ile Ser Asn Leu Gly Asp Asp Ala Tyr Asp Ala Asn
        660                 665                 670

Val Ser Phe Asn Val Ser Arg Glu Leu Phe Phe Ile Asn Met Trp Gln
        675                 680                 685

Lys Glu Glu Met Gly Ile Ser Cys Glu Leu Leu Glu Ser Asp Phe Leu
        690                 695                 700

Lys Cys Ser Val Gly Phe Pro Phe Met Arg Ser Lys Ser Lys Tyr Glu
705                 710                 715                 720

Phe Ser Val Ile Phe Asp Thr Ser His Leu Ser Gly Glu Glu Val
            725                 730                 735

Leu Ser Phe Ile Val Thr Ala Gln Ser Gly Asn Thr Glu Arg Ser Glu
        740                 745                 750

Ser Leu His Asp Asn Thr Leu Val Leu Met Val Pro Leu Met His Glu
        755                 760                 765

Val Asp Thr Ser Ile Thr Gly Ile Met Ser Pro Thr Ser Phe Val Tyr
770                 775                 780

Gly Glu Ser Val Asp Ala Ala Asn Phe Ile Gln Leu Asp Asp Leu Glu
785                 790                 795                 800

Cys His Phe Gln Pro Ile Asn Ile Thr Leu Gln Val Tyr Asn Thr Gly
            805                 810                 815

Pro Ser Thr Leu Pro Gly Ser Ser Val Ser Ile Ser Phe Pro Asn Arg
        820                 825                 830

Leu Ser Ser Gly Gly Ala Glu Met Phe His Val Gln Glu Met Val Val
        835                 840                 845

Gly Gln Glu Lys Gly Asn Cys Ser Phe Gln Lys Asn Pro Thr Pro Cys
850                 855                 860

Ile Ile Pro Gln Glu Gln Glu Asn Ile Phe His Thr Ile Phe Ala Phe
865                 870                 875                 880

Phe Thr Lys Ser Gly Arg Lys Val Leu Asp Cys Glu Lys Pro Gly Ile
            885                 890                 895
```

```
Ser Cys Leu Thr Ala His Cys Asn Phe Ser Ala Leu Ala Lys Glu Glu
            900                 905                 910

Ser Arg Thr Ile Asp Ile Tyr Met Leu Leu Asn Thr Glu Ile Leu Lys
            915                 920                 925

Lys Asp Ser Ser Val Ile Gln Phe Met Ser Arg Ala Lys Val Lys
    930                 935                 940

Val Asp Pro Ala Leu Arg Val Val Glu Ile Ala His Gly Asn Pro Glu
945                 950                 955                 960

Glu Val Thr Val Val Phe Glu Ala Leu His Asn Leu Glu Pro Arg Gly
                965                 970                 975

Tyr Val Val Gly Trp Ile Ile Ala Ile Ser Leu Leu Val Gly Ile Leu
            980                 985                 990

Ile Phe Leu Leu Leu Ala Val Leu Leu Trp Lys Met Gly Phe Phe Arg
            995                 1000                1005

Arg Arg Tyr Lys Glu Ile Ile Glu Ala Glu Lys Asn Arg Lys Glu
    1010                1015                1020

Asn Glu Asp Ser Trp Asp Trp Val Gln Lys Asn Gln
    1025                1030                1035

<210> SEQ ID NO 37
<211> LENGTH: 1036
<212> TYPE: PRT
<213> ORGANISM: Mus musculus

<400> SEQUENCE: 37

Met Gly Gly Pro Ala Gly Leu Arg Thr Gly Ala Gly Gly Leu Arg Ala
1               5                   10                  15

Leu Leu Leu Ala Leu Val Ala Ala Gly Val Pro Ala Gly Ala Tyr Asn
            20                  25                  30

Leu Asp Ala Gln Arg Pro Val Arg Phe Gln Gly Pro Ser Gly Ser Phe
        35                  40                  45

Phe Gly Tyr Ala Val Leu Glu His Phe His Glu Asn Thr Arg Trp Val
    50                  55                  60

Leu Val Gly Ala Pro Lys Ala Asp Ser Lys Tyr Ser Thr Ser Val Lys
65                  70                  75                  80

Ser Pro Gly Ala Val Phe Lys Cys Arg Val His Thr Asn Pro Glu Arg
                85                  90                  95

Arg Cys Thr Glu Leu Asp Met Ala Arg Gly Arg Thr Arg Gly Ala Pro
            100                 105                 110

Cys Gly Lys Thr Cys Arg Gly Asp Arg Asp Glu Trp Met Gly Val
        115                 120                 125

Ser Leu Ala Arg Gln Pro Arg Ala Asp Gly Arg Val Leu Ala Cys Ala
    130                 135                 140

His Arg Trp Lys Asn Ile Tyr Tyr Glu Ala Asp Gln Ile Leu Ala His
145                 150                 155                 160

Gly Phe Cys Tyr Leu Ile Pro Ser Asn Leu Gln Ala Lys Gly Lys Val
                165                 170                 175

Leu Ile Pro Cys Tyr Glu Glu Tyr Lys Lys Tyr Gly Glu Glu His
            180                 185                 190

Gly Ser Cys Gln Ala Gly Ile Ala Gly Phe Phe Thr Glu Glu Leu Val
        195                 200                 205

Val Met Gly Ala Pro Gly Ser Phe Tyr Trp Ala Gly Thr Leu Lys Val
    210                 215                 220

Leu Asn Leu Thr Asp Asn Thr Tyr Phe Lys Leu Asn Asp Glu Ala Ile
225                 230                 235                 240
```

```
Met Asn Arg Arg Tyr Thr Tyr Leu Gly Tyr Ala Val Thr Ala Gly His
            245                 250                 255

Phe Ser His Pro Ser Ile Thr Asp Val Val Gly Gly Ala Pro Gln Asp
            260                 265                 270

Glu Gly Ile Gly Lys Val Tyr Ile Phe Arg Ala Asp Arg Arg Ser Gly
            275                 280                 285

Thr Leu Val Lys Ile Phe Gln Ala Ser Gly Lys Lys Met Gly Ser Tyr
            290                 295                 300

Phe Gly Ser Ser Leu Cys Ala Val Asp Leu Asn Met Asp Gly Leu Ser
305                 310                 315                 320

Asp Leu Leu Val Gly Ala Pro Met Phe Ser Glu Ile Arg Asp Glu Gly
                325                 330                 335

Gln Val Thr Val Tyr Leu Asn Gln Gly His Gly Ala Leu Glu Glu Gln
                340                 345                 350

Leu Thr Leu Thr Gly Asp Ala Ala Tyr Asn Ala His Phe Gly Glu Ser
            355                 360                 365

Ile Ala Asn Leu Gly Asp Ile Asp Asp Asp Gly Phe Pro Asp Val Ala
        370                 375                 380

Val Gly Ala Pro Lys Glu Glu Asp Phe Ala Gly Ala Val Tyr Ile Tyr
385                 390                 395                 400

His Gly Asp Ala Asn Gly Ile Val Pro Lys Tyr Ser Met Lys Leu Ser
                405                 410                 415

Gly Arg Arg Leu Asn Pro Thr Leu Arg Met Phe Gly Gln Ser Ile Ser
            420                 425                 430

Gly Gly Ile Asp Met Asp Gly Asn Gly Tyr Pro Asp Val Thr Ile Gly
        435                 440                 445

Ala Phe Leu Ser Asp Ser Val Val Leu Arg Ala Arg Pro Val Ile
    450                 455                 460

Thr Val Asp Val Ser Ile Phe Leu Pro Gly Ser Ile Asn Ile Thr Ala
465                 470                 475                 480

Pro Gln Cys His Asp Gly Gln Gln Pro Val Asn Cys Leu Asn Val Thr
                485                 490                 495

Val Cys Phe Arg Phe His Gly Lys Asn Val Pro Gly Glu Ile Gly Leu
            500                 505                 510

Asn Tyr Asn Leu Thr Ala Asp Val Ala Gln Lys Glu Lys Gly Gln Leu
        515                 520                 525

Pro Arg Val Tyr Phe Val Leu Phe Gly Glu Thr Ala Gly Gln Val Ser
    530                 535                 540

Glu Arg Leu Gln Leu Ser His Met Asp Glu Val Cys His His Tyr Val
545                 550                 555                 560

Ala His Val Lys Arg Arg Val Gln Asp Val Ile Ser Pro Ile Val Phe
                565                 570                 575

Glu Ala Ala Tyr Ser Leu Asp Glu His Val Met Gly Glu Glu Asp Arg
            580                 585                 590

Glu Leu Pro Asp Leu Thr Pro Val Leu Arg Trp Lys Lys Gly Gln Arg
        595                 600                 605

Ile Ser Gln Lys Asn Gln Thr Val Phe Glu Arg Asn Cys Gln Ser Glu
    610                 615                 620

Asp Cys Ala Ala Asp Leu Gln Leu Arg Gly Lys Leu Leu Leu Ser Ser
625                 630                 635                 640

Val Asp Glu Lys Thr Pro His Leu Ala Leu Gly Ala Val Lys Asn Ile
                645                 650                 655

Ser Leu Asn Ile Ser Ile Ser Asn Leu Gly Asp Asp Ala Tyr Asp Ala
```

```
                    660                 665                 670
Asn Val Ser Phe Asn Val Ser Arg Glu Leu Phe Phe Ile Asn Met Trp
                675                 680                 685
Gln Lys Glu Glu Met Gly Ile Ser Cys Glu Leu Leu Glu Ser Asp Phe
            690                 695                 700
Leu Lys Cys Ser Val Gly Phe Pro Phe Met Arg Ser Lys Ser Lys Tyr
705                 710                 715                 720
Glu Phe Ser Val Ile Phe Asp Thr Ser His Leu Ser Gly Glu Glu Glu
                725                 730                 735
Ile Leu Ser Phe Ile Val Thr Ala Gln Ser Gly Asn Leu Glu Arg Ser
                740                 745                 750
Glu Ala Leu His Asp Asn Thr Leu Thr Leu Thr Val Pro Leu Val His
                755                 760                 765
Glu Val Asp Thr Ser Ile Thr Gly Ile Val Ser Pro Thr Ser Phe Val
            770                 775                 780
Tyr Gly Glu Ser Val Asp Ala Ser Asn Phe Ile Gln Leu Asp Asp Gln
785                 790                 795                 800
Glu Cys His Phe Gln Pro Val Asn Ile Thr Leu Gln Val Tyr Asn Met
                805                 810                 815
Gly Pro Ser Thr Leu Pro Gly Ser Ser Val Ser Ile Ser Phe Pro Ser
            820                 825                 830
Arg Leu Ser Pro Gly Gly Ala Glu Met Phe Gln Val Gln Asp Met Val
            835                 840                 845
Val Ser Gln Glu Lys Gly Asn Cys Ser Leu Gln Arg Asn Pro Thr Pro
850                 855                 860
Cys Ile Ile Pro Gln Glu Gln Glu Asn Ile Phe His Thr Ile Phe Ala
865                 870                 875                 880
Phe Phe Ser Lys Ser Gly Arg Lys Val Leu Asp Cys Glu Lys Pro Gly
                885                 890                 895
Ser Phe Cys Leu Thr Leu His Cys Asn Leu Ser Ala Leu Pro Lys Glu
                900                 905                 910
Glu Ser Arg Thr Ile Asn Leu Tyr Met Leu Leu Asn Thr Glu Ile Leu
            915                 920                 925
Lys Lys Asp Ser Ser Ser Val Ile Gln Phe Met Ala Arg Ala Lys Val
        930                 935                 940
Lys Val Glu Pro Ala Leu Arg Val Val Glu Ile Ala Asn Gly Asn Pro
945                 950                 955                 960
Glu Glu Thr Leu Val Val Phe Glu Ala Leu His Asn Leu Glu Pro Arg
                965                 970                 975
Gly Tyr Val Val Gly Trp Ile Ile Ala Ile Ser Leu Leu Val Gly Ile
            980                 985                 990
Leu Ile Phe Leu Leu Leu Ala Val  Leu Leu Trp Lys Met  Gly Phe Phe
        995                 1000                1005
Arg Arg  Arg Tyr Lys Glu Ile  Ile Glu Ala Glu Lys  Asn Arg Lys
        1010                1015                1020
Glu Asn  Glu Asp Gly Trp Asp  Trp Val Gln Lys Asn  Gln
    1025                1030                1035

<210> SEQ ID NO 38
<211> LENGTH: 430
<212> TYPE: PRT
<213> ORGANISM: Homo sapiens

<400> SEQUENCE: 38

Tyr Asn Val Asp Thr Glu Ser Ala Leu Leu Tyr Gln Gly Pro His Asn
```

```
            1               5               10              15
Thr Leu Phe Gly Tyr Ser Val Val Leu His Ser His Gly Ala Asn Arg
                20              25              30

Trp Leu Leu Val Gly Ala Pro Thr Ala Asn Trp Leu Ala Asn Ala Ser
                35              40              45

Val Ile Asn Pro Gly Ala Ile Tyr Arg Cys Arg Ile Gly Lys Asn Pro
 50              55              60

Gly Gln Thr Cys Glu Gln Leu Gln Leu Gly Ser Pro Asn Gly Glu Pro
 65              70              75              80

Cys Gly Lys Thr Cys Leu Glu Glu Arg Asp Asn Gln Trp Leu Gly Val
                85              90              95

Thr Leu Ser Arg Gln Pro Gly Glu Asn Gly Ser Ile Val Thr Cys Gly
                100             105             110

His Arg Trp Lys Asn Ile Phe Tyr Ile Lys Asn Glu Asn Lys Leu Pro
                115             120             125

Thr Gly Gly Cys Tyr Gly Val Pro Pro Asp Leu Arg Thr Glu Leu Ser
                130             135             140

Lys Arg Ile Ala Pro Cys Tyr Gln Asp Tyr Val Lys Lys Phe Gly Glu
145             150             155             160

Asn Phe Ala Ser Cys Gln Ala Gly Ile Ser Ser Phe Tyr Thr Lys Asp
                165             170             175

Leu Ile Val Met Gly Ala Pro Gly Ser Ser Tyr Trp Thr Gly Ser Leu
                180             185             190

Phe Val Tyr Asn Ile Thr Thr Asn Lys Tyr Lys Ala Phe Leu Asp Lys
                195             200             205

Gln Asn Gln Val Lys Phe Gly Ser Tyr Leu Gly Tyr Ser Val Gly Ala
                210             215             220

Gly His Phe Arg Ser Gln His Thr Thr Glu Val Val Gly Gly Ala Pro
225             230             235             240

Gln His Glu Gln Ile Gly Lys Ala Tyr Ile Phe Ser Ile Asp Glu Lys
                245             250             255

Glu Leu Asn Ile Leu His Glu Met Lys Gly Lys Lys Leu Gly Ser Tyr
                260             265             270

Phe Gly Ala Ser Val Cys Ala Val Asp Leu Asn Ala Asp Gly Phe Ser
                275             280             285

Asp Leu Leu Val Gly Ala Pro Met Gln Ser Thr Ile Arg Glu Glu Gly
                290             295             300

Arg Val Phe Val Tyr Ile Asn Ser Gly Ser Gly Ala Val Met Asn Ala
305             310             315             320

Met Glu Thr Asn Leu Val Gly Ser Asp Lys Tyr Ala Ala Arg Phe Gly
                325             330             335

Glu Ser Ile Val Asn Leu Gly Asp Ile Asp Asn Asp Gly Phe Glu Asp
                340             345             350

Val Ala Ile Gly Ala Pro Gln Glu Asp Leu Gln Gly Ala Ile Tyr
                355             360             365

Ile Tyr Asn Gly Arg Ala Asp Gly Ile Ser Ser Thr Phe Ser Gln Arg
                370             375             380

Ile Glu Gly Leu Gln Ile Ser Lys Ser Leu Ser Met Phe Gly Gln Ser
385             390             395             400

Ile Ser Gly Gln Ile Asp Ala Asp Asn Asn Gly Tyr Val Asp Val Ala
                405             410             415

Val Gly Ala Phe Arg Ser Asp Ser Ala Val Leu Leu Arg Thr
                420             425             430
```

<210> SEQ ID NO 39
<211> LENGTH: 430
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Phe Asn Leu Asp Ala Glu Arg Pro Val His Phe Gln Gly Pro Ala Asp
1               5                   10                  15

Ser Phe Phe Gly Tyr Ala Val Leu Glu His Phe His Asp Asn Thr Arg
            20                  25                  30

Trp Val Leu Val Gly Ala Pro Lys Ala Asp Ser Lys Tyr Ser Pro Ser
        35                  40                  45

Val Lys Ser Pro Gly Ala Val Phe Lys Cys Arg Val His Thr Asn Pro
    50                  55                  60

Asp Arg Arg Cys Thr Glu Leu Asp Met Ala Arg Gly Lys Asn Arg Gly
65                  70                  75                  80

Thr Ser Cys Gly Lys Thr Cys Arg Glu Asp Arg Asp Glu Trp Met
                85                  90                  95

Gly Val Ser Leu Ala Arg Gln Pro Lys Ala Asp Gly Arg Val Leu Ala
            100                 105                 110

Cys Ala His Arg Trp Lys Asn Ile Tyr Tyr Glu Ala Asp His Ile Leu
        115                 120                 125

Pro His Gly Phe Cys Tyr Ile Ile Pro Ser Asn Leu Gln Ala Lys Gly
    130                 135                 140

Arg Thr Leu Ile Pro Cys Tyr Glu Glu Tyr Lys Lys Lys Tyr Gly Glu
145                 150                 155                 160

Glu His Gly Ser Cys Gln Ala Gly Ile Ala Gly Phe Phe Thr Glu Glu
                165                 170                 175

Leu Val Val Met Gly Ala Pro Gly Ser Phe Tyr Trp Ala Gly Thr Ile
            180                 185                 190

Lys Val Leu Asn Leu Thr Asp Asn Thr Tyr Leu Lys Leu Asn Asp Glu
        195                 200                 205

Val Ile Met Asn Arg Arg Tyr Thr Tyr Leu Gly Tyr Ala Val Thr Ala
    210                 215                 220

Gly His Phe Ser His Pro Ser Thr Ile Asp Val Val Gly Gly Ala Pro
225                 230                 235                 240

Gln Asp Lys Gly Ile Gly Lys Val Tyr Ile Phe Arg Ala Asp Arg Arg
                245                 250                 255

Ser Gly Thr Leu Ile Lys Ile Phe Gln Ala Ser Gly Lys Lys Met Gly
            260                 265                 270

Ser Tyr Phe Gly Ser Ser Leu Cys Ala Val Asp Leu Asn Gly Asp Gly
        275                 280                 285

Leu Ser Asp Leu Leu Val Gly Ala Pro Met Phe Ser Glu Ile Arg Asp
    290                 295                 300

Glu Gly Gln Val Thr Val Tyr Ile Asn Arg Gly Asn Gly Ala Leu Glu
305                 310                 315                 320

Glu Gln Leu Ala Leu Thr Gly Asp Gly Ala Tyr Asn Ala His Phe Gly
                325                 330                 335

Glu Ser Ile Ala Ser Leu Asp Asp Leu Asp Asn Asp Gly Phe Pro Asp
            340                 345                 350

Val Ala Ile Gly Ala Pro Lys Glu Asp Asp Phe Ala Gly Ala Val Tyr
        355                 360                 365
```

Ile Tyr His Gly Asp Ala Gly Gly Ile Val Pro Gln Tyr Ser Met Lys
370                 375                 380

Leu Ser Gly Gln Lys Ile Asn Pro Val Leu Arg Met Phe Gly Gln Ser
385                 390                 395                 400

Ile Ser Gly Gly Ile Asp Met Asp Gly Asn Gly Tyr Pro Asp Val Thr
                405                 410                 415

Val Gly Ala Phe Met Ser Asp Ser Val Val Leu Leu Arg Ala
                420                 425                 430

<210> SEQ ID NO 40
<211> LENGTH: 430
<212> TYPE: PRT
<213> ORGANISM: Mus musculus

<400> SEQUENCE: 40

Tyr Asn Leu Asp Ala Gln Arg Pro Val Arg Phe Gln Gly Pro Ser Gly
1               5                   10                  15

Ser Phe Phe Gly Tyr Ala Val Leu Glu His Phe His Asp Asn Thr Arg
                20                  25                  30

Trp Val Leu Val Gly Ala Pro Lys Ala Asp Ser Lys Tyr Ser Thr Ser
            35                  40                  45

Val Lys Ser Pro Gly Ala Val Phe Lys Cys Arg Val His Thr Asn Pro
50                  55                  60

Asp Arg Arg Cys Thr Glu Leu Asp Met Ala Arg Gly Thr Arg Gly
65                  70                  75                  80

Ala Pro Cys Gly Lys Thr Cys Arg Gly Asp Arg Asp Glu Trp Met
                85                  90                  95

Gly Val Ser Leu Ala Arg Gln Pro Arg Ala Asp Gly Arg Val Leu Ala
            100                 105                 110

Cys Ala His Arg Trp Lys Asn Ile Tyr Tyr Glu Ala Asp His Ile Leu
        115                 120                 125

Pro His Gly Phe Cys Tyr Leu Ile Pro Ser Asn Leu Gln Ala Lys Gly
    130                 135                 140

Lys Val Leu Ile Pro Cys Tyr Glu Glu Tyr Lys Lys Tyr Gly Glu
145                 150                 155                 160

Glu His Gly Ser Cys Gln Ala Gly Ile Ala Gly Phe Phe Thr Glu Glu
                165                 170                 175

Leu Val Val Met Gly Ala Pro Gly Ser Phe Tyr Trp Ala Gly Thr Leu
            180                 185                 190

Lys Val Leu Asn Leu Thr Asp Asn Thr Tyr Phe Lys Leu Asn Asp Glu
        195                 200                 205

Ala Ile Met Asn Arg Arg Tyr Thr Tyr Leu Gly Tyr Ala Val Thr Ala
    210                 215                 220

Gly His Phe Ser His Pro Ser Ile Thr Asp Val Val Gly Gly Ala Pro
225                 230                 235                 240

Gln Asp Glu Gly Ile Gly Lys Val Tyr Ile Phe Arg Ala Asp Arg Arg
                245                 250                 255

Ser Gly Thr Leu Val Lys Ile Phe Gln Ala Ser Gly Lys Lys Met Gly
            260                 265                 270

Ser Tyr Phe Gly Ser Ser Leu Cys Ala Val Asp Leu Asn Met Asp Gly
        275                 280                 285

Leu Ser Asp Leu Leu Val Gly Ala Pro Met Phe Ser Glu Ile Arg Asp
    290                 295                 300

Glu Gly Gln Val Thr Val Tyr Leu Asn Gln Gly His Gly Ala Leu Glu
305                 310                 315                 320

```
Glu Gln Leu Thr Leu Thr Gly Asp Ala Ala Tyr Asn Ala His Phe Gly
            325             330             335

Glu Ser Ile Ala Asn Leu Gly Asp Ile Asp Asp Gly Phe Pro Asp
            340             345             350

Val Ala Val Gly Ala Pro Lys Glu Glu Asp Phe Ala Gly Ala Val Tyr
        355             360             365

Ile Tyr His Gly Asp Ala Asn Gly Ile Val Pro Lys Tyr Ser Met Lys
        370             375             380

Leu Ser Gly Arg Arg Leu Asn Pro Thr Leu Arg Met Phe Gly Gln Ser
385                 390             395                     400

Ile Ser Gly Gly Ile Asp Met Asp Gly Asn Gly Tyr Pro Asp Val Thr
                405             410             415

Ile Gly Ala Phe Leu Ser Asp Ser Val Val Leu Leu Arg Ala
            420             425             430
```